United States Patent
Bezdek et al.

(10) Patent No.: US 8,712,797 B1
(45) Date of Patent: Apr. 29, 2014

(54) METHODS AND SYSTEM FOR PROVIDING DRUG PRICING INFORMATION FROM MULTIPLE PHARMACY BENEFIT MANAGERS (PBMS)

(71) Applicant: GoodRx, Inc., Santa Monica, CA (US)

(72) Inventors: Trevor Zachary Bezdek, Los Angeles, CA (US); Douglas Joseph Hirsch, Los Angeles, CA (US); Scott Andrew Marlette, Los Angeles, CA (US); William Raymond McClure, Santa Monica, CA (US); Andrew David Slutsky, Santa Monica, CA (US)

(73) Assignee: GoodRx, Inc., Santa Monica, CA (US)

( * ) Notice: Subject to any disclaimer, the term of this patent is extended or adjusted under 35 U.S.C. 154(b) by 0 days.

(21) Appl. No.: 14/160,208

(22) Filed: Jan. 21, 2014

Related U.S. Application Data

(60) Provisional application No. 61/769,617, filed on Feb. 26, 2013.

(51) Int. Cl.
   *G06Q 50/00* (2012.01)
   *G06Q 10/00* (2012.01)
   *G06F 19/00* (2011.01)

(52) U.S. Cl.
   CPC ............... *G06Q 50/00* (2013.01); *G06Q 10/00* (2013.01); *G06F 19/328* (2013.01)
   USPC .................................... 705/2; 705/3; 705/400

(58) Field of Classification Search
   CPC ....... G06Q 50/22; G06Q 10/00; G06F 19/328
   USPC .............................................. 705/2, 3, 4, 400
   See application file for complete search history.

(56) References Cited

U.S. PATENT DOCUMENTS

| | | | | |
|---|---|---|---|---|
| 7,860,732 | B2 * | 12/2010 | Elizabeth et al. | 705/3 |
| 8,296,164 | B2 * | 10/2012 | Oscar et al. | 705/2 |
| 8,380,540 | B1 * | 2/2013 | Smith et al. | 705/3 |
| 8,447,628 | B2 * | 5/2013 | Kalies, Jr. | 705/2 |
| 8,457,992 | B1 * | 6/2013 | Harding et al. | 705/4 |
| 2001/0037216 | A1 * | 11/2001 | Oscar et al. | 705/2 |
| 2004/0078234 | A1 * | 4/2004 | Tallal, Jr. | 705/2 |
| 2004/0117323 | A1 * | 6/2004 | Mindala | 705/400 |
| 2007/0043589 | A1 * | 2/2007 | Warren et al. | 705/2 |

(Continued)

OTHER PUBLICATIONS

Google patents search, Feb. 27, 2014.*

(Continued)

*Primary Examiner* — Dilek B Cobanoglu
(74) *Attorney, Agent, or Firm* — Knobbe Martens Olson & Bear LLP

(57) ABSTRACT

A system according to certain aspects of the disclosure provides drug pricing information from multiple PBMs to users. For example, the system may obtain, calculate, and/or estimate drug prices that are available under contracts or agreements between PBMs and various pharmacies. These prices may be prices of drugs for purchase at the various pharmacies. In response to requests for prices of particular drugs, the system can display relevant prices. For example, the system displays a price for each pharmacy chain and/or displays prices for a particular geographical area. The users can compare the prices for a particular drug and determine which pharmacy they would like to purchase the drug from. The system can provide a discount coupon that allows the users to purchase the drug at the price listed by the system at the selected pharmacy.

20 Claims, 8 Drawing Sheets

(56) References Cited

U.S. PATENT DOCUMENTS

2012/0173263 A1* 7/2012 Nease et al. .................. 705/2
2012/0185263 A1* 7/2012 Emert ........................... 705/2
2013/0013335 A1* 1/2013 Oscar et al. ................... 705/2
2013/0054258 A1* 2/2013 Cohan et al. .................. 705/2

OTHER PUBLICATIONS

Google search, Feb. 28, 2014.*

* cited by examiner

FIG. 8

METHODS AND SYSTEM FOR PROVIDING DRUG PRICING INFORMATION FROM MULTIPLE PHARMACY BENEFIT MANAGERS (PBMS)

INCORPORATION BY REFERENCE TO ANY PRIORITY APPLICATIONS

This application claims the benefit of U.S. Provisional Application No. 61/769,617, filed Feb. 26, 2013, the entire content of which is incorporated herein by reference. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to managing medical benefits and, more particularly, to managing pharmacy benefits to reduce costs.

SUMMARY

According to one aspect, a method of displaying prices for drugs from a plurality of pharmacy benefit managers is provided. The method can include providing a user interface using a computer processor. The method may further include receiving from the user interface information identifying a first drug. The method can additionally include obtaining a first set of prices for the first drug that is associated with a first pharmacy benefit manager (PBM), wherein a pharmacy benefit manager processes a claim relating to a drug and has an agreement with a pharmacy relating to a price of one or more drugs, the first set of prices comprising at least one price for the first drug and each price in the first set of prices being determined by an agreement between the first PBM and a pharmacy. The method can further include obtaining a second set of prices for the first drug that is associated with a second pharmacy benefit manager, the second set of prices comprising at least one price for the first drug and each price in the second set of prices being determined by an agreement between the second PBM and a pharmacy. The method can also include displaying in the user interface at least a portion of the first set of prices and the second set of prices.

In some embodiments, the method may further include receiving a selection of a price from the at least a portion of the first set of prices and the second set of prices displayed in the user interface. The method may also include generating a discount card or a discount coupon that provides access to the selected price for a purchase of the first drug at a pharmacy associated with the selected price. In certain embodiments, the selected price may not be available to a customer for the purchase of the first drug at the pharmacy from a PBM associated with the selected price without the discount card or the discount coupon. In some embodiments, the selected price may be provided under an agreement with the PBM associated with the selected price, and the agreement may be different from an agreement between the PBM associated with the selected price and the pharmacy associated with the selected price. In some embodiments, the discount card or the discount coupon may include an identification number that is recognized by a PBM associated with the selected price.

In certain embodiments, the first PBM can administer claims relating to a first health insurance plan, and an agreement between the first PBM and a first pharmacy may specify a price of the first drug for a member of the first health insurance plan and a first price of the first drug for a customer that is not a member of the first health insurance plan. The first set of prices may include the first price of the first drug for a customer that is not a member of the first health insurance plan. The second PBM can administer claims relating to a second health insurance plan, and an agreement between the second PBM and a second pharmacy may specify a price of the first drug for a member of the second health insurance plan and a second price of the first drug for a customer that is not a member of the second health insurance plan. The second set of prices may include the second price of the first drug for a customer that is not a member of the second health insurance plan. In some embodiments, the method can further include displaying in the user interface the first price of the first drug for a customer that is not a member of the first health insurance plan. The method can also include, in response to selection of the first price received from the user interface, generating a discount coupon for a purchase of the first drug at the first price at the first pharmacy.

In some embodiments, the information identifying the first drug may include a name of the first drug. In certain embodiments, the method may further include receiving from the user interface location information. The method may also include, prior to the displaying at least a portion of the first set of prices and the second set of prices, filtering the first set of prices and the second set of prices based on the location information.

In certain embodiments, the at least one price in the first set of prices may be obtained by using an API provided by the first PBM. In some embodiments, the at least one price in the first set of prices can be obtained based on pricing rules for the first drug provided by the first PBM.

In some embodiments, the first set of prices may include a first price for the first drug determined by an agreement between the first PBM and a first pharmacy and the second set of prices may include a second price for the first drug determined by an agreement between the second PBM and the first pharmacy. The displaying at least a portion of the first set of prices and the second set of prices of the method can include comparing the first price for the first drug and the second price for the first drug, and displaying lower of the first price for the first drug and the second price for the first drug.

According to another aspect, a system is provided for displaying prices for drugs from a plurality of pharmacy benefit managers. The system may include computer hardware comprising one or more computer processors. The system may also include a module executing on the one or more computer processors. The module can be configured to receive a request for one or more prices for a first drug. The module may be further configured to obtain a first set of prices for the first drug that is associated with a first pharmacy benefit manager (PBM), wherein a pharmacy benefit manager processes a claim relating to a drug and has an agreement with a pharmacy relating to a price of one or more drugs, the first set of prices comprising at least one price for the first drug and each price in the first set of prices being determined by an agreement between the first PBM and a pharmacy. The module may be further configured to obtain a second set of prices for the first drug that is associated with a second pharmacy benefit manager, the second set of prices comprising at least one price for the first drug and each price in the second set of prices being determined by an agreement between the second PBM and a pharmacy. The module can be further configured to display in the user interface at least a portion of the first set of prices and the second set of prices.

In some embodiments, the module may be further configured to receive a selection of a price from the at least a portion of the first set of prices and the second set of prices displayed in the user interface, and generate a discount card or a discount coupon that provides access to the selected price for a purchase of the first drug at a pharmacy associated with the selected price. In certain embodiments, the selected price may not be available to a customer for the purchase of the first drug at the pharmacy from a PBM associated with the selected price without the discount card or the discount coupon. In some embodiments, the selected price may be provided under an agreement with the PBM associated with the selected price, and the agreement may be different from an agreement between the PBM associated with the selected price and the pharmacy associated with the selected price. In certain embodiments, the discount card or the discount coupon may include an identification number that is recognized by a PBM associated with the selected price.

In certain embodiments, the first PBM can administer claims relating to a first health insurance plan, and an agreement between the first PBM and a first pharmacy may specify a price of the first drug for a member of the first health insurance plan and a first price of the first drug for a customer that is not a member of the first health insurance plan. The first set of prices may include the first price of the first drug for a customer that is not a member of the first health insurance plan. The second PBM can administer claims relating to a second health insurance plan, and an agreement between the second PBM and a second pharmacy may specify a price of the first drug for a member of the second health insurance plan and a second price of the first drug for a customer that is not a member of the second health insurance plan. The second set of prices may include the second price of the first drug for a customer that is not a member of the second health insurance plan. In some embodiments, the module may be further configured to display in the user interface the first price of the first drug for a customer that is not a member of the first health insurance plan, and in response to selection of the first price received from the user interface, generate a discount coupon for a purchase of the first drug at the first price at the first pharmacy.

In some embodiments, the first set of prices may include a first price for the first drug determined by an agreement between the first PBM and a first pharmacy, and the second set of prices may include a second price for the first drug determined by an agreement between the second PBM and the first pharmacy. The module may perform the displaying at least a portion of the first set of prices and the second set of prices at least in part by comparing the first price for the first drug and the second price for the first drug, and displaying lower of the first price for the first drug and the second price for the first drug.

According to certain aspects, a method of displaying prices for drugs from a plurality of pharmacy benefit managers is provided. The method may include providing a user interface using a computer processor. The method can further include receiving information identifying a first drug from the user interface. The method may additionally include obtaining a first set of prices for the first drug that is associated with a first pharmacy benefit manager (PBM), wherein a pharmacy benefit manager processes a claim relating to a drug and has an agreement with one or more pharmacies relating to a price of one or more drugs, the first set of prices comprising at least one price for the first drug and each price in the first set of prices being determined by an agreement between the first PBM and a pharmacy. The method can further include obtaining a second set of prices for the first drug that is associated with a second pharmacy benefit manager, the second set of prices comprising at least one price for the first drug and each price in the second set of prices being determined by an agreement between the second PBM and a pharmacy. The method may also include ranking the at least one price for the first drug in the first set of prices for the first drug and the at least one price for the first drug in the second set of prices for the first drug in an order that is different from lowest to highest. The method can also include displaying a price from the ranking in the user interface.

In some embodiments, the ranking of the method may further include, in response to determining that the at least one price for the first drug in the first set of prices is higher than or equal to the at least one price for the first drug in the second set of prices, ranking the at least one price in the first set of prices higher than the at least one price in the second set of prices. In certain embodiments, the ranking the at least one price in the first set of prices higher than the at least one price in the second set of prices may be performed in response to determining that a difference between the at least one price for the first drug in the first set of prices and the at least one price for the first drug in the second set of prices does not exceed a threshold value. In some embodiments, wherein the ranking the at least one price in the first set of prices higher than the at least one price in the second set of prices may be based on a first acceptance rate associated with the at least one price in the first set of prices and a second acceptance rate associated with the at least one price in the second set of prices. In certain embodiments, a higher ranked price from the ranking is displayed in the user interface. In some embodiments, the method may further include determining a preferred order for ranking prices from the first PBM and prices from the second PBM. The preferred order may indicate that prices from the first PBM are to be ranked higher than prices from the second PBM.

In certain embodiments, a first percentage may indicate a portion of prices from the first PBM to be displayed in the user interface. A second percentage may indicate a portion of prices from the second PBM to be displayed in the user interface. The ranking may include ranking the at least one price for the first drug in the first set of prices and the at least one price for the first drug in the second set of prices based at least in part on the first percentage and the second percentage. In some embodiments, the second percentage may be linked to a threshold value for ranking prices from the first PBM over the second PBM such that adjusting the second percentage adjusts the threshold value and adjusting the threshold value adjusts the second percentage.

In some embodiments, the first PBM can administer claims relating to a first health insurance plan, and an agreement between the first PBM and a first pharmacy may specify a price of the first drug for a member of the first health insurance plan and a first price of the first drug for a customer that is not a member of the first health insurance plan. The first set of prices may include the first price of the first drug for a customer that is not a member of the first health insurance plan. The second PBM can administer claims relating to a second health insurance plan, and an agreement between the second PBM and a second pharmacy may specify a price of the first drug for a member of the second health insurance plan and a second price of the first drug for a customer that is not a member of the second health insurance plan. The second set of prices may include the second price of the first drug for a customer that is not a member of the second health insurance plan. In certain embodiments, the method can further include displaying in the user interface the first price of the first drug for a customer that is not a member of the first health insurance plan. The method can also include, in response to selection of the first price received from the user interface, generating a discount coupon for a purchase of the first drug at the first price at the first pharmacy.

According to other aspects, a system of displaying prices for drugs from a plurality of pharmacy benefit managers is provided. The system can include computer hardware comprising one or more computer processors. The system may further include a module executing on the one or more computer processors. The module can be configured to provide a user interface using a computer processor. The module may be further configured to receive information identifying a first drug from the user interface. The module may also be configured to obtain a first set of prices for the first drug that is associated with a first pharmacy benefit manager (PBM), wherein a pharmacy benefit manager processes a claim relating to a drug and has an agreement with one or more pharmacies relating to a price of one or more drugs, the first set of prices comprising at least one price for the first drug and each price in the first set of prices being determined by an agreement between the first PBM and a pharmacy. The module may additionally be configured to obtain a second set of prices for the first drug that is associated with a second pharmacy benefit manager, the second set of prices comprising at least one price for the first drug and each price in the second set of prices being determined by an agreement between the second PBM and a pharmacy. The module can be further configured to rank the at least one price for the first drug in the first set of prices for the first drug and the at least one price for the first drug in the second set of prices for the first drug in an order that is different from lowest to highest. The module may also be configured to display a price from the ranking in the user interface.

In some embodiments, the module may perform the ranking at least in part by, in response to determining that the at least one price for the first drug in the first set of prices is higher than or equal to the at least one price for the first drug in the second set of prices, ranking the at least one price in the first set of prices higher than the at least one price in the second set of prices. In certain embodiments, the module may perform the ranking the at least one price in the first set of prices for the first drug higher than the at least one price in the second set of prices for the first drug at least in part in response to determining that a difference between the at least one price for the first drug in the first set of prices and the at least one price for the first drug in the second set of prices does not exceed a threshold value. In some embodiments, the module may perform the ranking the at least one price in the first set of prices higher than the at least one price in the second set of prices based at least in part on a first acceptance rate associated with the at least one price in the first set of prices and a second acceptance rate associated with the at least one price in the second set of prices. In certain embodiments, a higher ranked price from the ranking may be displayed in the user interface. In some embodiments, the module may be further configured to determine a preferred order for ranking prices from the first PBM and prices from the second PBM. The preferred order may indicate that prices from the first PBM are to be ranked higher than prices from the second PBM.

In certain embodiments, a first percentage may indicate a portion of prices from the first PBM to be displayed in the user interface. A second percentage may indicate a portion of prices from the second PBM to be displayed in the user interface. The module may perform the ranking at least in part by ranking the at least one price for the first drug in the first set of prices and the at least one price for the first drug in the second set of prices based at least in part on the first percentage and the second percentage. In some embodiments, the second percentage may be linked to a threshold value for ranking prices from the first PBM over the second PBM such that adjusting the second percentage adjusts the threshold value and adjusting the threshold value adjusts the second percentage.

In some embodiments, the first PBM can administer claims relating to a first health insurance plan, and an agreement between the first PBM and a first pharmacy may specify a price of the first drug for a member of the first health insurance plan and a first price of the first drug for a customer that is not a member of the first health insurance plan. The first set of prices may include the first price of the first drug for a customer that is not a member of the first health insurance plan. The second PBM can administer claims relating to a second health insurance plan, and an agreement between the second PBM and a second pharmacy may specify a price of the first drug for a member of the second health insurance plan and a second price of the first drug for a customer that is not a member of the second health insurance plan. The second set of prices may include the second price of the first drug for a customer that is not a member of the second health insurance plan. In some embodiments, the module may be further configured to display in the user interface the first price of the first drug for a customer that is not a member of the first health insurance plan, and in response to selection of the first price received from the user interface, generate a discount coupon for a purchase of the first drug at the first price at the first pharmacy.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 8 illustrates another embodiment of a user interface for providing drug prices from various Pharmacy Benefit Managers.

DETAILED DESCRIPTION

Figure 1:
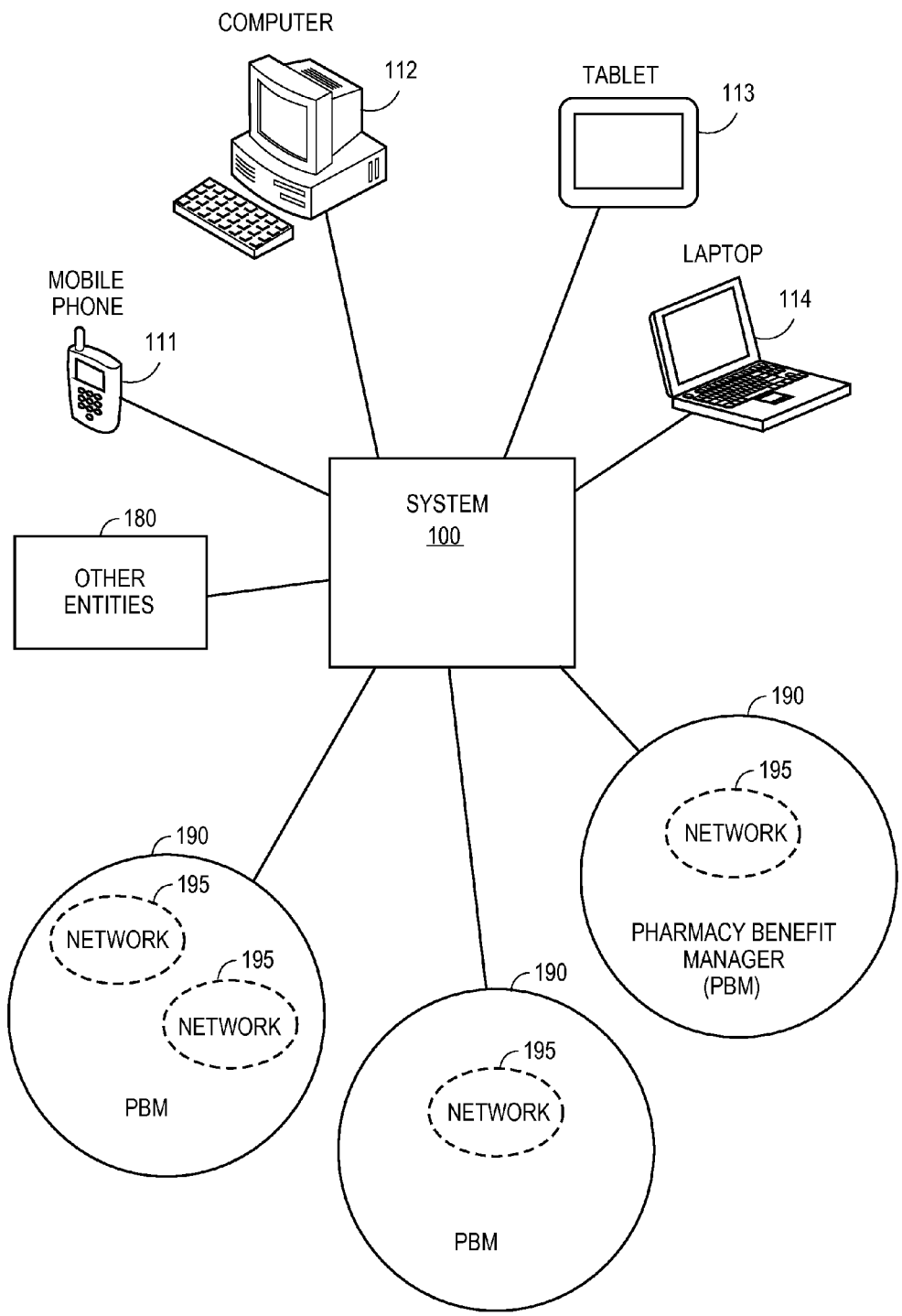
FIG. 1 illustrates an overview of an example system for providing drug prices from multiple Pharmacy Benefit Managers (PBMs), according to one aspect of the disclosure.

The disclosure provided in the following pages describes examples of some embodiments of the invention. The designs, figures, and description are non-limiting examples of some embodiments of the invention. Other embodiments of the system may or may not include the features disclosed herein. Moreover, disclosed advantages and benefits may apply to only some embodiments of the invention, and should not be used to limit the scope of the invention.

Health care costs in the United States have risen dramatically over the past several decades. To reduce such costs, Pharmacy Benefit Managers (PBMs) have been used to process claims for prescription drug benefits. PBMs are typically entities that are independent of the benefit provider, e.g. an insurance company, and contract with the benefit provider to process claims for pharmacy benefits.

The distribution channels for prescription drugs are, in many cases, separated from the payment channels. For example, a patient may be diagnosed by a physician as having a condition that requires medication. The physician then decides on a drug appropriate for treatment of the diagnosed condition and prepares a prescription for an appropriate drug. The patient then takes the prescription to a pharmacy for dispensing of the prescription drugs. If the patient has a prescription drug benefit, e.g., through health insurance coverage, the pharmacist will utilize their computer system to access the PBMs computer system to apply the negotiated charge. Consequently, the patient may not be aware of the differing costs for the drug by different PBMs and/or at different pharmacies.

Furthermore, different PBMs operate under different agreements with pharmacies. For example, the price for a drug associated with one PBM can often differ significantly with respect to a second PBM. Accordingly, one PBM may provide a lower cost on one drug than other PBMs, but have a much higher cost for other drugs. Indeed, prices for the same drugs can vary significantly among different PBMs. Some PBMs also offer discount cards that enable a consumer to access their rate agreements with a pharmacy. These discount cards have consumer prices that differ by drug and by pharmacy, and even different discount cards from the same PBM can have different consumer prices.

Many Americans assume that the solution is simply to obtain pay for health insurance or Medicare, and thereby utilize a particular PBM, and then show up at any pharmacy counter. While this may have been true years ago, it is no longer reality. Insurance companies are increasing prescription drug deductibles and patient co-pays while reducing the numbers and quantities of the drugs that they will pay for. Meanwhile, hundreds of medicines can be purchased for cash for less than an insurance co-pay.

In order to address these and other challenges, a system according to certain aspects of the disclosure provides drug pricing information from multiple PBMs to users. For example, the system may obtain, calculate, and/or estimate drug prices that are available under contracts or agreements between PBMs and various pharmacies. These prices may be prices of drugs for purchase at the various pharmacies. The system can process the drug pricing information such that it can be readily provided to users in response to requests for prices of particular drugs. In response to such requests, the system can display relevant prices. For example, the system displays a price for each pharmacy chain and/or displays prices for a particular geographical area. The users can compare the prices for a particular drug and determine which pharmacy they would like to purchase the drug from. The system can provide a discount coupon that allows the users to purchase the drug at the price listed by the system at the selected pharmacy.

The system can aggregate drug pricing information from multiple PBMs and present the data to the users in a simple and easy-to-digest manner. As such, the system can provide users with convenience and valuable information that can translate into savings in time and costs.

In one embodiment of the inventive system, the system identifies the lower-cost pharmacy for a particular drug. A user enters information about a prescription such as the name of the drug (generic or brand-name), the form and the dosage. The user also provides a location (city, state or ZIP), and the system identifies the prices the user can obtain at both local and mail order pharmacies for a variety of dosages and quantities for that prescription.

The system searches the fee schedules associated with multiple PBM discount cards to identify lower-cost prices. Because different pharmacies accept different discount cards and offer different consumer prices on those discount cards, the system identifies which pharmacies will accept discount cards with the more advantageous cost savings. The system then offers discount cards, presented to the user as free discount coupons that are printable, as well as available for use on a mobile device, from a variety of providers which gives the user access to the PBM discounted prices. The discount coupon identifies the relevant PBM and the associated price.

In one embodiment, the system contracts with multiple PBMs such that the system can pass the PBM savings onto the users. The users do not need to contract directly with the PBMs. Rather, the system is associated with multiple PBMs and prints the appropriate PBM discount coupon that a user can print and provide to a particular pharmacy.

In one embodiment, the system works with multiple discount drug card providers that issue a discount card that provides access to pharmacy discounts at retail pharmacies. The system calculates the price for a particular drug, dosage, form, or quantity at a given pharmacy using each of the discount cards. It does this either by performing a mock adjudication of a claim, or by calculating the price based on pricing rules, such as discount from lists such as Average Wholesale Price ("AWP"), or Maximum Allowable Cost ("MAC") lists.

The system typically then displays the lowest price among the set of multiple discount cards, allowing the system to provide lower prices than existing discount card products. The system, in turn, receives compensation from the discount drug card providers for prescription drug fills that take place using a particular card.

The system typically shows consumers the drug card with the lowest consumer price. In many cases though, multiple cards will provide similar consumer prices, even though the compensation paid by the discount card providers to the system may differ substantially. In order to maximize revenue, the system ranks different cards such that for the same consumer price, there is an order in which they are displayed.

In addition, an administrator can specify an offset, such that if an offset were set at 0.10, the higher ranked card would be displayed versus a lower ranked card as long as the consumer price for the higher ranked card was no more than 0.10 higher than the lower ranked card.

FIG. 1 illustrates an overview of an example system 100 for providing drug prices from multiple Pharmacy Benefit Managers 190, according to one aspect of the disclosure. The system 100 may be configured to provide drug pricing information from multiple PBMs 190. The system 100 may communicate with multiple PBMs 190, for example, in order to obtain information relating to prices of various drugs. As explained above, a PBM 190 may administer and/or process claims relating to drugs (e.g., prescription drugs). A PBM 190 may negotiate with one or more pharmacies regarding prices for various drugs (e.g., under a contract or agreement with a pharmacy). For example, PBM 1 and Pharmacy A can form an agreement on how much PBM 1 will compensate Pharmacy A for certain drugs and/or how much Pharmacy A will charge customers for certain drugs.

A pharmacy generally contracts with multiple PBMs 190 for prices for various drugs. A pharmacy may be a part of a pharmacy chain that owns or is associated with multiple locations. For example, large pharmacy chains like CVS, Walgreens, Rite-Aid, etc. have multiple retail locations across the U.S. In such case, the pharmacy chain generally contracts with the PBMs 190 for drug prices, and the retail locations of the pharmacy chain use the prices under the contract.

A PBM 190 generally administers and processes claims associated with a health insurance plan, such as Anthem, Aetna, etc. For example, a PBM 190 and a pharmacy determines under an agreement what the price for a particular drug will be for a health plan. The members of the health plan are charged a certain price for the drug under the agreement between the PBM 190 and the pharmacy. Often, as part of the agreement between the PBM 190 and the pharmacy, the PBM 190 may also negotiate drug prices for people who are not members of the health plan. These customers are unfunded because the health plan is not paying for these customers for their prescriptions. These customers may be referred to as "unfunded group" to facilitate explanation. Prices for unfunded group under agreements between PBMs 190 and pharmacies may be referred to as "unfunded drug prices."

Although the unfunded group may not get the benefit of the prices available to members of the health plan, the unfunded drug prices may still be much less than drug prices cash customers pay. "Cash customers" may refer to customers who purchase a drug without any discounted pricing (e.g., available through a health plan), and the prices the cash customers pay may be referred to as "cash prices." The unfunded drug prices may be available through a pharmacy discount card or a discount card. Such discount cards may provide discounts on prescription drugs and/or generic drugs. In certain embodiments, the system 100 can obtain and provide information about unfunded drug pricing under various contracts between PBMs 190 and pharmacies.

A PBM 190 can administer one or more networks 195 within the PBM 190. A "network" may refer to one particular set of prices. For example, a pharmacy can have multiple networks 195 within the PBM 190. In such case, the pharmacy may have one set of prices with the PBM 190 under one network and another set of prices with the PBM 190 under a different network. The price for the same drug may be different from one set of prices to another set of prices.

An entity associated with the system 100 may negotiate and enter into an agreement with a PBM 190, which is separate from the agreements between the PBM 190 and pharmacies, in order to access prices between the PBM 190 and pharmacies. For example, the entity may obtain or determine unfunded drug prices under various agreements between the PBM 190 and the pharmacies. In some cases, the prices available to the entity under the separate agreement with the PBMs 190 may not be the exact prices agreed upon by PBMs 190 and pharmacies, but similar prices. In such case, the system 100 may provide users with prices that are similar or close to the prices agreed upon between the PBMs 190 and the pharmacies.

The system 100 may also communicate with other entities 180, such as a pharmacy. For example, the system 100 can obtain drug pricing information from a particular pharmacy. In some embodiments, the system 100 processes prescription drug claims and may communicate with a pharmacy's system. In certain embodiments, some of the functions provided by the system 100 are integrated into an electronic medical record (EMR) system, and the system 100 may communicate with the EMR system.

The system 100 can provide a user interface to receive input from a user and/or to display information to the user. For example, the user can enter information for obtaining drug pricing information through the user interface. The user interface can display drug pricing information and/or other information to the user. The user interface may be provided on various computing devices, such as a mobile phone 111, a computer 112, a tablet 113, a laptop 114, etc.

Figure 2:
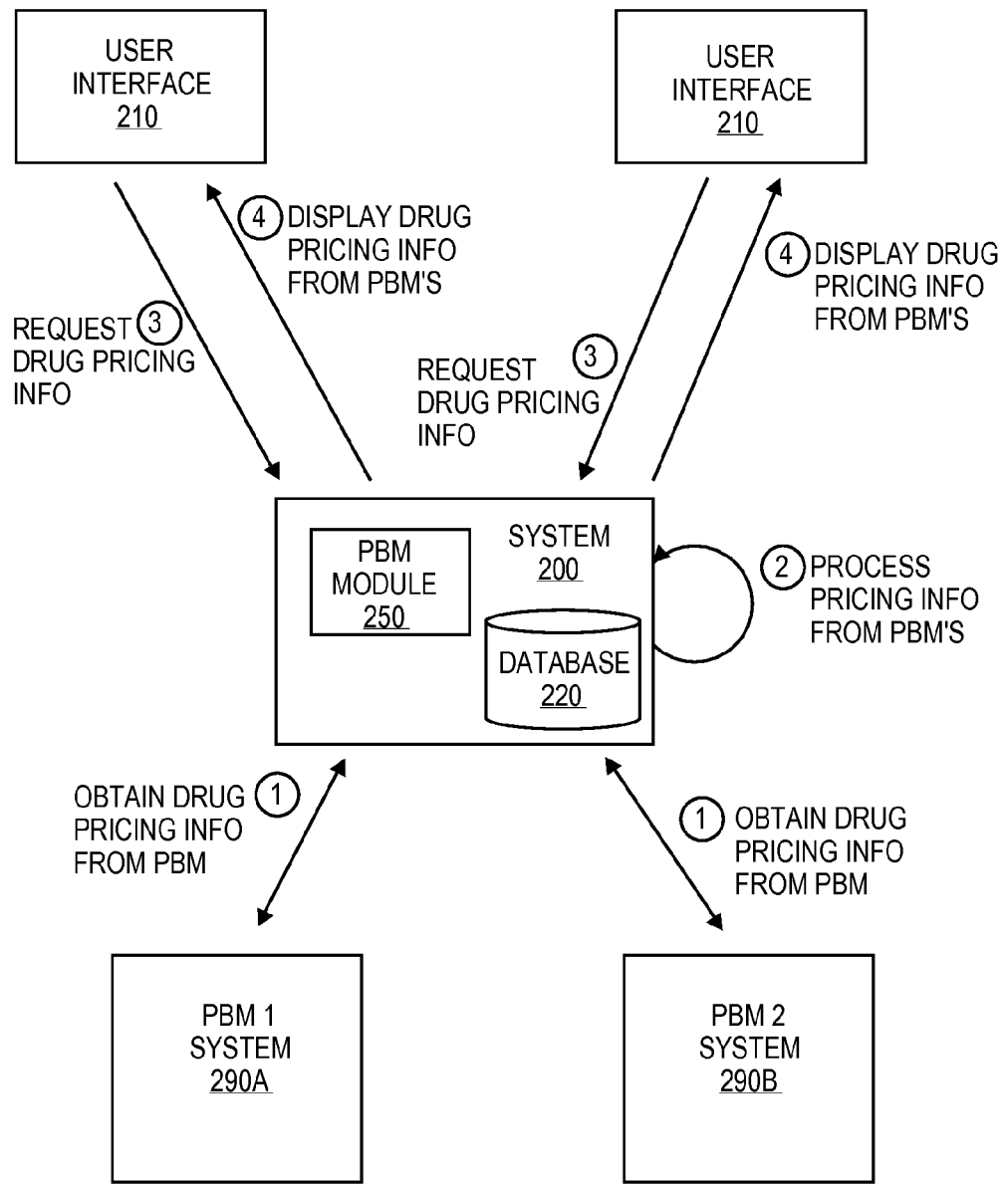
FIG. 2 illustrates an example data flow diagram for providing drug prices from multiple Pharmacy Benefit Managers, according to one aspect of the disclosure.

FIG. 2 illustrates an example data flow diagram for providing drug prices from multiple Pharmacy Benefit Managers, according to one aspect of the disclosure. FIG. 2 illustrates a system 200 that can be configured to provide drug prices from multiple PBMs. The system 200 may be similar to the system 100 in FIG. 1.

The system 200 can communicate with the systems of PBMs. For example, the system 200 communicates with the PBM 1 system 290a and the PBM 2 system 290b. Such communication may occur through an interface, such as an application programming interface (API). The system 200 can include one or more components that may be configured to provide drug prices from multiple PBMs. For example, in FIG. 2, the system 200 includes a PBM Module 250 that can perform or execute functions relating to providing drug prices from multiple PBMs. The system 200 may include one or more other components as appropriate in order to implement the functionality of providing drug prices from multiple PBMs. The system 200 may also include one or more databases 220 to store the drug pricing information. Any component and/or module of the system 200 can reside on one computing device or on separate computing devices.

FIG. 2 illustrates several data flow steps. Data flow steps are numbered for illustrative purposes and can occur or be performed in any order. One or more data flow steps may be omitted depending on the embodiment, and additional data flow steps can be added depending on the embodiment. All embodiments described in this disclosure may be implemented separately, together, or in combination. For example, one embodiment may include certain features of another embodiment. In addition, certain features discussed with respect to a particular embodiment may be omitted, and an embodiment may include additional features.

At data flow step 1, the system 200 obtains drug pricing information from a PBM system 290. As explained above, a PBM can negotiate and contract with one or more pharmacies on prices for various drugs. For example, PBM 1 and Pharmacy A agree that the price for Drug A is $20 and Drug B is $30. In some embodiments, a PBM administers multiple networks, and a pharmacy may have different price arrangements with the PBM under each network. For instance, PBM 1 administers claims for Network 1 and Network 2, and the price for Drug A for Pharmacy A under Network 1 is $20 and the price for Drug A for Pharmacy A under Network 2 is $15. In certain embodiments, the drug price information the system 200 obtains is unfunded drug prices. The price for Drug A for unfunded group might be $50, compared to $20 for members of a health plan.

The system 200 can obtain information relating to negotiated drug prices between a PBM and one or more pharmacies from the PBM system 290. These prices can be prices for purchase of various drugs at the one or more pharmacies. The system 200 may obtain the drug pricing information through an API. The PBM system 290 may provide an API, which includes functions that can be called by the system 200. The system 200 can call various functions to obtain relevant information. The system 200 may be able to perform mock adjudication of claims using the API in order to figure out drug prices charged by particular pharmacies. A mock adjudication can be performed by submitting information relating to drug name, form, dosage, quantity, pharmacy, etc. The National Drug Code (NDC) may be submitted for mock adjudication. The NDC can refer to a code that is used to identify a drug based on manufacturer, strength, package size, etc. The system 200 may try to determine the NDC for a drug at a particular pharmacy or pharmacy chain to submit for mock adjudication. In one embodiment, the system 200 submits the NDC of the drug, the quantity of the drug, and pharmacy information to the mock adjudication API, and the API returns the price for the drug.

In some cases, the system 200 may have access to actual claims data and determine the prices by analyzing the claims data. By analyzing the claims data, the system 200 can determine how much a pharmacy generally charges for a certain drug, form, dosage, quantity, with a particular PBM.

In some embodiments, the system 200 may not obtain drug pricing information from a PBM, but estimate or calculate the drug prices for a particular pharmacy with that PBM. In one example, a PBM provides a set of pricing rules for determining the price of various drugs. The pricing rules may be based on Average Wholesale Price (AWP). For instance, pricing rules may state that the price of a brand name drug is AWP−20%+dispensing fee and the price of a generic drug is AWP−70%+dispensing fee. Dispensing fee may refer to a fee associated with providing a drug (e.g., filling a prescription). The AWP data can be published by and available from third parties. The PBM may also provide a list of prices called the Maximum Allowable Cost (MAC) list. The MAC list can indicate maximum amounts the PBM pays for brand name drugs and generic drugs, and the prices in the MAC list may be exceptions to the pricing rules. The system 200 can calculate the price of a drug according to the pricing rules, compare it to the price in the MAC list, and provide lower of the two prices. Pricing rules may vary by pharmacy. If a pharmacy has more than one network with a PBM, the pricing rules can differ for each network with the PBM.

In certain embodiments, the system 200 can receive drug prices from sources other than PBMs. In one example, the system 200 receives the information directly from a source, such as a pharmacy. For instance, a pharmacy chain provides a list of the drug prices to the system 200.

In one embodiment, the system 200 obtains usual and customary (U&C) prices for drugs from various sources. A U&C price may refer to a cash price for a drug at a pharmacy. The system 200 can provide U&C prices for a drug, for example, when prices for the drug under agreements between the PBMs and pharmacies are not available. For instance, if a pharmacy does not have an unfunded price for a drug under an agreement with a PBM, the system 200 can display the pharmacy's U&C price for the drug instead.

At data flow step 2, the system 200 processes pricing information from the PBMs. In some embodiments, the system 200 obtains the information from the PBM systems 290 through an API, but the process of requesting and receiving the information may not be fast enough for real-time access. In such case, the system 200 may cache the drug pricing information, e.g., in the database 220. In one example, the mock adjudication results from the PBM API are stored in the database 220. The information processed by the system 200 can be stored in the database 220. FIG. 2 shows one database for illustrative purposes, but the system 200 can include two more databases.

In some embodiments, the pricing information obtained or determined at data flow step 1 may be stored in the database 220 prior to or without any processing by the system 200. For example, the system 200 may store any raw data before formatting or transforming the data according to the requirements of the system 200. In other embodiments, the system 200 may not perform any further processing with respect to the information obtained at data flow step 1.

At data flow step 3, the system 200 receives a request for drug pricing information from the user interface 210. The user interface 210 can be provided on a computing device or a display associated with the computing device. The computing device can be, for example, a mobile phone 111, a computer 112, a tablet 113, a laptop 114, etc. as shown in FIG. 1. The user may enter information relating to a drug (e.g., drug name) in the user interface 210, and the associated computing device can generate and send a request for drug pricing information to the system 200. The user interface 210 may be a web interface, a mobile application, or any other appropriate form of user interface.

The request can include any information identifying a drug that the user is interested in finding out prices for. For example, the request can include the name of a drug, and the user enters the name of the drug in the user interface 210. In one embodiment, the user clicks on an advertisement for a particular drug that links to the user interface 210, and the user interface 210 provides the name of the drug without the user having to enter the name. The request may also include location information. Some examples of location information include a zip code, city, address, etc. The location information can be information that the system 200 can use to narrow down the prices to those that are more relevant to a specific geographical area. The user may enter the location information in the user interface 210. In some embodiments, the location information can be determined based on other factors, such as an IP address, with or without user input.

The system 200 can search for or determine one or more prices for the requested drug. The prices may be prices from one or more pharmacies provided under agreements with different PBMs as obtained or determined at data flow step 1 and/or processed at data flow step 2. In some embodiments, the system 200 refers to the drug pricing information in the database 220 to provide relevant prices to the user. As explained with data flow steps 1 and 2, the drug pricing information may have been obtained through APIs provided by the PBMs and stored in the database 220. The drug pricing information could also have been extracted from analyzing actual claims data. Or the drug pricing information may have been calculated from pricing rules or estimated in other ways. In other embodiments, the system 200 obtains or determines the prices when a request from the user interface 210 is received. For instance, the prices are calculated according to the pricing rules when the request is received. Various methods of obtaining and/or determining prices, including the methods mentioned above, can be used together, separately, or in some combination. Information relating to prices or used in determining prices may be obtained or updated on demand (e.g., in real-time), periodically (e.g., on a regular basis, at a fixed interval, at a variable interval, etc.), etc. For example, the system 200 can obtain drug pricing information through the API, e.g., on a daily basis or as requested. In another example, the system 200 can obtain the AWP from a third party source, e.g., on a weekly basis. The system 200 may also receive new pricing rules or updates to pricing rules periodically (e.g., every month).

In one embodiment, requests for drug pricing information are received and stored in a queue. Some drug prices are obtained through the API from the PBM, but the speed of API may not be fast enough to provide the drug prices in real-time. In such case, the drug prices are cached. The first time a request is received for a specific drug, for example, for that day, the prices are obtained from the API and stored in the cache. For subsequent requests, the prices are provided from the cache.

At data flow step 4, the system 200 displays drug pricing information from PBMs in the user interface 210. The system 200 may display a list of prices for the drug for which pricing information was requested at data flow step 3. The system 200 can display prices from one or more pharmacies with multiple PBMs. As explained above, in general, a pharmacy contracts with multiple PBMs, and PBMs contract with multiple pharmacies for drug prices. Therefore, a pharmacy or a pharmacy chain may have multiple prices available for the same drug. In one embodiment, the system 200 displays prices from one or more pharmacies and displays multiple prices for each pharmacy.

In other embodiments, the system 200 displays prices for multiple pharmacies and displays one price for each pharmacy. For instance, the system 200 displays the lowest price for each pharmacy. In one example, Pharmacy A has a price for Drug A with PBM 1 and another price for Drug A with PBM 2. Supposing the price for Drug A with PBM 1 is $25 and the price for Drug A with PBM 2 is $15, the system 200 would display the price with PBM 2 since it is lower. Displaying the lowest price available from a pharmacy from multiple PBMs can be beneficial to the users since savings can be maximized. If there are two or more same lowest prices, the system 200 may select one to display arbitrarily or based on a variety of factors.

The prices displayed in the user interface 210 may be the prices for the most commonly purchased package of the drug. A drug can be manufactured and packaged in different ways. For instance, the same drug can be provided in different form (e.g., tablet, capsule, etc.), dosage (e.g., 10 mg, 20 mg, 40 mg), quantity (e.g., 10, 20, 50, etc.), etc. Form may refer to how the drug is delivered. Some examples of form include tablet, capsule, solution, tube, pump, etc. Dosage may refer to the amount of drug included in each unit or package and can indicate the strength of the drug. The amount can be indicated by weight (e.g., milligram (mg), gram (g), etc.), volume (e.g., milliliter (ml), etc.), etc. Quantity may refer to the number of units included in a package. The same drug may also be available as the brand version or generic version. The user interface 210 may display various options for indicating the package of the drug, and the user can select options corresponding to the package of the drug that the user wants. Such options can include, but is not limited to: generic vs. brand, form, dosage, quantity, etc. The system 200 can update the results to provide prices for the package of the drug selected by the user. The system 200 may also display other information relating to the drug in the user interface 210.

The system 200 can filter or narrow down the prices to be displayed based on the location information. In one embodiment, the results can be filtered based on the zip code entered by the user. Zip code is used as one example, but any other geographical or location indicator can be used, such as an address. The system 200 displays prices associated with pharmacy locations in proximity to the zip code. For example, proximity is determined to be within a default radius from the zip code. The user can select or adjust the radius for the pharmacy locations, and the results are updated accordingly. For example, the user can select 5, 10, 15, 20, 25 miles, etc. from the zip code. If a pharmacy has more than one location within the radius, the user interface 210 may display one price for the pharmacy, and the user can click on the price or another link to view information relating to the different locations. In one embodiment, the user interface 210 displays the addresses for the different locations.

In a certain embodiment, the user is not initially requested to enter location information. The system 200 displays prices for a drug at major pharmacy chains without filtering the prices for a geographical area. Then, the user may enter the location information, and the user interface 210 displays the prices relating to the location.

In some embodiments, the default or initial radius of pharmacy locations is determined by the system 200 based on factors like population density. For example, in highly populated cities like New York or Los Angeles, a smaller initial radius may be selected, for example, to avoid including too many results. The user can adjust the radius as appropriate in order to view prices for a larger area or a smaller area.

In certain embodiments, the system 200 displays a map of pharmacy locations within the default radius or user designated radius from the location information, along with the prices associated with these pharmacy locations. The map can initially display pharmacy locations in the default radius, and as the user changes the radius, the map can be updated to show pharmacy locations in the changed radius. For instance, if the radius is increased, the map zooms out and displays more locations, and if the radius is decreased, the map zooms in and displays fewer locations.

The system 200 can create an index to reduce the amount of time for searching for prices that are relevant to a specific location or geographical area. In one embodiment, the system 200 creates a two-dimensional ("2D") geospatial index. For example, when using a 2D geospatial index, the prices are stored with relevant 2D geospatial point(s), and the prices can be queried using the 2D geospatial index. In another embodiment, the system 200 creates a three-dimensional ("3D") geospatial index. A 3D geospatial index can have the spatial coordinates as the x-axis and the y-axis, and have the drug price as the z-axis.

The system 200 can also filter the prices to be displayed in the user interface 210 based on a variety of factors other than or including the location information. In one embodiment, the user interface 210 displays options relating to pharmacies, and the user can choose which types of pharmacies to view prices for. Some examples of pharmacy options or types include: 24-hour, mail order, home delivery, compounding, walk-in clinic, drive-up window, languages spoken, major chains, etc.

For a price displayed in the user interface 210, the system 200 can generate a discount coupon to purchase the drug at or close to the displayed price. A discount coupon can be for a specific pharmacy or a specific pharmacy location. In some embodiments, the prices displayed are unfunded prices available under agreements between PBMs and pharmacies for unfunded group. The system 200 provides a discount coupon in order to allow unfunded group to purchase the drug at unfunded prices.

A discount coupon for a drug can include the drug information and the price. The drug information may be the information relating to the specific package of the drug the user wants to purchase (e.g., name, form, dosage, quantity, etc.), as explained above. The discount coupon can include information, such as PCN number, bin number, group number, member ID, etc. PCN number and/or bin number can identify a PBM, and group number can identify the entity associated with the system 200. Member ID may be an identifier assigned by the system 200 under the agreement between the entity and the PBM identified by the PCN and/or bin number. In one embodiment, the member ID is used to identify the entity associated with the system 200. In another embodiment, a combination of group number and member ID is used to identify the entity. Information included on a discount coupon is explained further with respect to FIG. 6.

The discount coupon can be printed, emailed, sent by text message, etc. and presented at the pharmacy associated with the price for purchase of the drug at that price. In certain embodiments, the actual price may not be exactly the same as purchase price but close to the listed price. The pharmacist can enter the PCN number, bin number, group number, member ID, or any combination thereof to provide the listed price to the user. In some embodiments, the discount coupon includes a bar code, QR code, or another form of code that can be scanned by the pharmacist. Coupons can provide access to prices that were not previously available to a customer without the coupons. For example, discount coupons provide unfunded drug prices to customers who are not members of a health insurance plan covered by the agreement between a pharmacy and a PBM. In addition, the coupons allow customers to purchase at lower prices among the unfunded drug prices available from multiple PBMs.

The system 200 can also provide a discount card, in addition to discount coupons. A user can apply for a discount card which provides access to some or all of the prices provided by the system 200. Instead of printing a coupon for each price, the user can present the discount card, which a pharmacy can have in the user's record. The discount card then can work in a similar fashion as an insurance card, and the user can purchase any drugs that have unfunded prices under the PBM-pharmacy agreements at these prices. In some embodiments, a discount coupon functions as a discount card. For example, the pharmacist at a specific pharmacy enters the discount coupon in the user's record, and the user can access the prices provided by the system 200 for the pharmacy for subsequent purchases.

In one embodiment, the price of the drug for the discount coupon is dynamically adjusted. For example, if the cash price for a drug at a pharmacy is lower than the price of the drug provided by the system 200, the system 200 adjusts the price on the discount coupon to be lower than the cash price.

The system 200 may rank the drug prices from multiple PBMs prior to displaying drug prices in the user interface 210. The system 200 may display only some of the prices from the ranking process. Generally, if a pharmacy has multiple prices for the same drug under agreements with different PBMs, the system 200 displays one price for the pharmacy. In one embodiment, the system 200 ranks the prices for a pharmacy from lowest to highest and displays the lowest price. For example, a lower price is ranked higher than a higher price. In other embodiments, the system 200 ranks the prices for a pharmacy using methods other than lowest to highest. The system 200 may choose to display only one price from a ranking process in the user interface 210 (e.g., highest ranked or lowest ranked price from the ranking process, etc.).

In one embodiment, the system 200 may rank a higher price from one PBM as higher than, or before, a lower price from another PBM. The system 200 may do so based on various factors. One such factor can be acceptance rate of a price or prices from a PBM at pharmacies. Another factor can be a partnership with a particular PBM. For instance, a PBM may provide more accurate information regarding prices or provide additional benefits that can be passed on to consumers. The system 200 may rank a higher price higher than a lower price if the difference between the higher price and the lower price does not exceed a threshold value (or is less than the threshold value). Ranking a price higher than another price can refer to placing the price before the other price in a sequence. The threshold can be set low such that the impact on the price to the user is minimal. For example, the threshold can be set to $0.10, $0.20, etc. In general, the threshold value is less than $1. The same threshold value may be set for all drugs provided by a PBM, or a different threshold value can be set for a group of drugs or an individual drug provided by a PBM.

The system 200 may rank prices from PBMs based on the in-store acceptance rate of prices or coupons from a PBM at a particular pharmacy. An acceptance rate may refer to the rate at which a price or a coupon from a PBM is accepted at a specific pharmacy. The acceptance rate of a price can be affected by a variety of attributes or factors, such as format of member ID and/or group ID, programmatic blocking by pharmacies, system and/or software used by pharmacies, etc. Often, the information on the coupon is entered manually into the pharmacy system by a pharmacist and can involve human error. Accordingly, prices from PBMs that use simpler identifiers may have a higher success rate of being accepted at the pharmacy locations. The identifiers can include the member ID, group ID, bin number, PCN number, etc. By considering the acceptance rates associated with prices from a PBM, the system 200 can provide a price that is more likely to translate into a discount for the user.

In one example, the in-store acceptance rate of prices from PBM 1 is 85%, and the in-store acceptance rate of prices from PBM 2 is 70%. The price for Drug A at Pharmacy A under PBM 1 is $25.10, and the price for Drug A at Pharmacy A under PBM 2 is $25. The threshold value for ranking a higher paying PBM price higher is set to $0.10. Because PBM 1 has a higher acceptance rate, but the price differential between the PBM 1 price and the PBM 2 price is $0.10 and does not exceed the threshold value, the system 200 ranks the PBM 1 price higher than the PBM 2 price. The system 200 displays PBM 1 price for Pharmacy A in the user interface 210.

In some embodiments, the system 200 may rank a price based on either the acceptance rate or the threshold, but not both. For example, the system 200 can rank a higher price having a higher acceptance rate higher than a lower price having a lower acceptance rate without applying a threshold to the price difference (e.g., when the acceptance rate of a lower price is very low). A lower price that has an acceptance rate of 15% may not be as beneficial to the user as a higher price that has an acceptance rate of 95%. Or the system 200 can rank a higher price over a lower price if the price difference does not exceed a threshold without considering the acceptance rate (e.g., based on another factor, such as order of preference for PBMs).

Prices with low acceptance rates or prices not being accepted may be excluded in the ranking process. For example, if a particular class of drugs is not being processed at certain pharmacies or by certain PBMs, the prices for these drugs would not be displayed even if they are lower prices. Prices having low acceptance rates (including those not being accepted) may not be included in the ranking, or they may be ranked but excluded from being displayed. The system 200 may define a threshold value for acceptance rates. Prices having acceptable rates that do not meet the threshold value (e.g., less than the threshold value, or less than or equal to the threshold value, depending on the embodiment) may be excluded from ranking and may not be displayed in the user interface 210. For example, if the acceptance rate threshold is 50%, and the acceptance rate of a price is 5%, the price is not included in the ranking. The acceptance rate threshold value may be applied prior to ranking or subsequent to ranking. For instance, the system 200 can perform the ranking and determine whether the ranked prices to be displayed meet the acceptance rate threshold value (e.g., whether the prices have acceptance rates that are greater than the threshold value, or greater than or equal to the threshold value, depending on the embodiment). Or the system 200 can eliminate prices that do not meet the acceptance rate threshold value (e.g., prices having acceptance rates that are less than the threshold value, or less than or equal to the threshold value, depending on embodiment) before the ranking. An acceptance rate threshold value may be defined for each drug, for a group of drugs (e.g., particular class of drugs), for all drugs, etc.

Information relating to acceptance rates may be provided by the PBM or determined by the system 200. Acceptance rate information may be available for each drug, for a group of drugs (e.g., particular class of drugs), or for all drugs. In one example, the acceptance rate can be provided for each drug. In some cases, one acceptance rate value may be provided for all drugs (or some drugs); the PBMs may not differentiate between individual drugs in determining the acceptance rate. If a PBM has multiple networks, the acceptance rate information can be provided for each network.

In one embodiment, the system 200 compares the number of coupons printed and/or viewed and the number of in-pharmacy redemption of coupons in order to determine the acceptance rate. If a coupon for a drug is frequently viewed or printed by users, but has a low in-store conversion rate, this could flag that there is an issue with acceptance of the price or coupon. For instance, the coupon for Drug A with the price from PBM 1 at Pharmacy A may be printed or viewed 100 times, but only result in 45 redemptions at Pharmacy A. In such case, the acceptance rate of the price from PBM 1 for Drug A at Pharmacy A is 45%. On the other hand, the coupon for Drug A with the price from PBM 2 at Pharmacy A may be printed or viewed 100 times, and result in 95 redemptions at Pharmacy A. The acceptance rate of the price from PBM 2 for Drug A at Pharmacy A is 95%. The acceptance rate can be based on the number of prints and/or views and the number of redemptions for a particular period of time (e.g., monthly, biweekly, weekly, daily, etc.). The print and/or view count and redemption count for coupons (or prices) from different PBMs may be available from historical data. The print and/or view count and redemption count for coupons (or prices) may also be available from current data (e.g., from the same day, week, etc.).

In certain embodiments, if there are more than two PBMs, the system 200 can list the PBMs in order of preference and determine multiple threshold values for listing one PBM over another PBM. For instance, there are three PBMs (PBM 1, PBM 2, PBM 3), and the preference for listing prices from these PBMs are in the order of PBM 3, PBM 1, and PBM 2. The system 200 defines a threshold value for listing prices from PBM 3 over prices from PBM 1 and a threshold value for listing prices from PBM 1 over prices from PBM 2. Accordingly, the system 200 can rank prices from multiple PBMs for a pharmacy, given that the price difference between one PBM and another PBM does not exceed the designated threshold.

In one embodiment, the system 200 may determine whether to rank a price from one PBM higher than a price from another PBM based on the percentage of prices to show for a specific PBM. Referring to the example above, if there are three PBMs (PBM 1, PBM 2, PBM 3), the system 200 designates a percentage of prices to display from PBM 1, a percentage of prices to display from PBM 2, and a percentage of prices to display from PBM 3. For instance, the percentage for PBM 3 can be 50%, the percentage for PBM 1 can be 30%, and the percentage for PBM 2 can be 20%. In certain embodiments, the percentage for a PBM is linked to the threshold value for listing one PBM over another. For example, the percentage for displaying prices from PBM 1 is linked to the threshold value for listing PBM 3 over PBM 1 such that when the threshold value is changed, the percentage is updated. If the percentage is changed, the threshold value is updated.

The system 200 can also choose to rank the prices from different PBMs based on various factors other than or in addition to acceptance rate and PBM partnership, such as compensation by a PBM to the entity for a purchase of a drug (e.g., filling a prescription). Such ranking may sort the prices in an order that is different from a lowest-to-highest ranking.

In this manner, the system 200 can allow users to purchase drugs at prices that were not previously available to them by utilizing the discount coupons. The entity associated with system 200 can enter into agreements with the PBMs and pass on the savings to users. By obtaining and/or determining drug pricing information from multiple PBMs and selecting lower prices available from each PBM to provide to the users, the entity can create a new discount network of prices. The entity can also make unfunded drug prices available to the users, which can save a significant amount of money. Often, the cash price of a drug is multiple times the unfunded price of the drug. Users without health insurance plans can benefit from reduced prices almost all of the time. And even users with health insurance plans can benefit when a drug is not covered under their plans or the system 200 provides better prices for the drug. As explained above, the system 200 can provide a convenient and easy-to-use user interface 210, making it simple for users to find the information they are looking for.

In some embodiments, the system 200 is integrated into an EMR system. The system 200 can provide an API that can be called by the EMR system. For example, the EMR system calls one or more functions of the API to determine which pharmacy to send a patient's prescription to. Or the EMR system can present a link to a patient so that the patient can choose a specific pharmacy location based on the drug pricing information.

The system 200 may also display other information relating to a drug in the user interface 210. The system 200 could also provide additional information that may be helpful to users. Such information is explained in more detail with respect to FIGS. 7 and 8.

Figure 3:
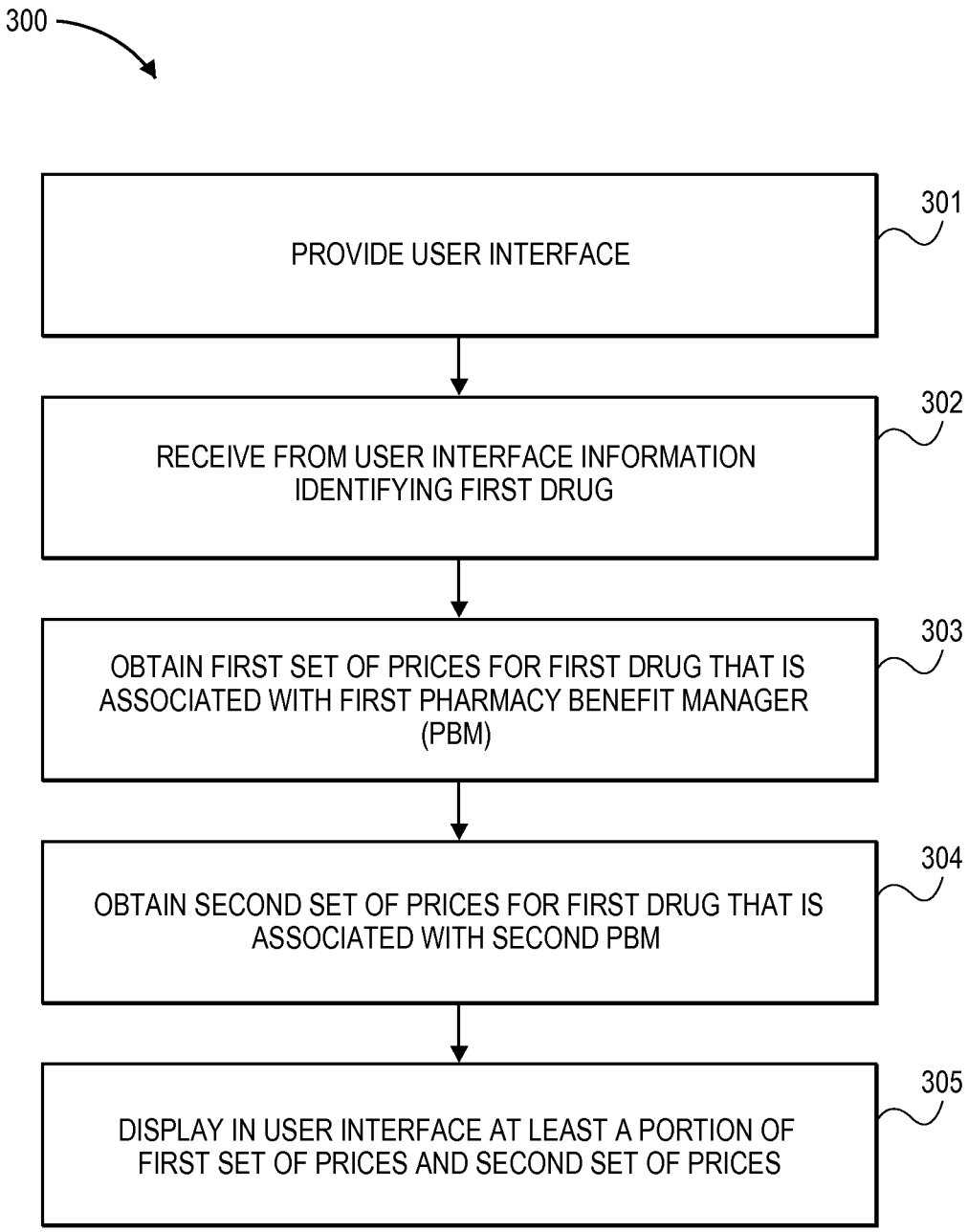
FIG. 3 illustrates one embodiment of an example process for displaying drug prices from multiple for Pharmacy Benefit Managers.

FIG. 3 illustrates one embodiment of an example process 300 for displaying drug prices from multiple for PBMs. The process 300 is described with respect to the system 200 of FIG. 2. However, one or more of the steps of process 300 may be implemented by other systems, such as the system 100 described in FIG. 1. The process 300 can be implemented by any one of, or a combination of, the components of the system 200 (e.g., the PBM module 250). Further details regarding certain aspects of at least some of steps of the process 300 are described in greater detail above with reference to FIGS. 1 and 2.

At block 301, the system 200 provides a user interface 210 for providing drug pricing information. Users can request pricing information about a specific drug via the user interface 210. For example, the user can enter the name of the drug and the user's zip code in the user interface 210, and send a request for pricing information.

At block 302, the system 200 receives from the user interface 210 information identifying a first drug. The information can include the name of the drug. The system 200 can also receive location information from the user interface 210.

At block 303, the system 200 obtains a first set of prices for the first drug that is associated with a first pharmacy benefit manager (PBM). A PBM may process a claim relating to a drug and have an agreement with a pharmacy relating to a price of one or more drugs (e.g., by a contract). The first set of prices can include at least one price for the first drug, and each price in the first set of prices can be determined by an agreement between the first PBM and a pharmacy. Each price in the first set of prices may be a price for purchase of the first drug at the pharmacy associated with the price.

In one embodiment, the at least one price in the first set of prices is obtained by performing of a mock adjudication of a claim relating to the first drug using an API provided by the first PBM. In another embodiment, the at least one price in the first set of prices is obtained based on pricing rules for the first drug provided by the first PBM.

At block 304, the system 200 obtains a second set of prices for the first drug that is associated with a second PBM. The second set of prices can include at least one price for the first drug, and each price in the second set of prices can be determined by an agreement between the second PBM and a pharmacy. Each price in the second set of prices may be a price for purchase of the first drug at the pharmacy associated with the price. The pharmacy for the first set of the prices and the second set of prices may be the same pharmacy or different pharmacies.

In one embodiment, similar to block 303, the at least one price in the second set of prices is obtained by performing of a mock adjudication of a claim relating to the first drug using an API provided by the second PBM. In another embodiment, the at least one price in the second set of prices is obtained based on pricing rules for the first drug provided by the second PBM.

In some embodiments, the first PBM may administer claims relating to a health insurance plan, and an agreement between the first PBM and a pharmacy may specify a price of the first drug for a member of the health insurance plan and a price of the first drug for a customer that is not a member of the health insurance plan. The first set of prices can include the price of the first drug for a customer that is not a member of the health insurance plan, which may be referred to as the "non-member price."

Similarly, the second PBM may administer claims relating to a health insurance plan. The health insurance plan may be the same plan as or a different plan from the one administered by the first PBM. An agreement between the second PBM and a pharmacy may specify a price of the first drug for a member of the health insurance plan and a price of the first drug for a customer that is not a member of the health insurance plan. The second set of prices can include the price of the first drug for a customer that is not a member of the health insurance plan. The pharmacy may be the same pharmacy with which the first PBM has an agreement or a different pharmacy from the pharmacy with which the first PBM has an agreement. In these embodiments, the system 200 may display the non-member price for the first drug included in the first set of prices, or the non-member price for the first drug included in the second set of prices.

At block 305, the system 200 displays in the user interface 210 at least a portion of the first set of prices and the second set of prices. The first set of prices and the second set of prices each include at least one price for the same drug, but the system 200 may not list a price from each set. For example, if the price of the first drug in the first set and the price of the first drug in the second set are for the same pharmacy, the system 200 can list one of the prices (e.g., the lower price).

In one embodiment, the first set of prices includes a price for the first drug determined by an agreement between the first PBM and a pharmacy, and the second set of prices includes a second price for the first drug determined by an agreement between the second PBM and the pharmacy. The system 200 compares the first price for the first drug and the second price for the first drug, and displays lower of the first price for the first drug and the second price for the first drug. In another embodiment, as explained above, if an agreement between a PBM and a pharmacy specifies a non-member price for the first drug, the system 200 displays the non-member price in the user interface 210.

In some embodiments, the system 200 filters the first set of prices and the second set of prices based on the location information prior to displaying at least a portion of the first set of prices and the second set of prices in the user interface 210.

The process 300 can include fewer, more, or different blocks than those illustrated in FIG. 3 without departing from the spirit and scope of the description. Moreover, it will be appreciated by those skilled in the art and others that some or all of the functions described in this disclosure may be embodied in software executed by one or more processors of the disclosed components and mobile communication devices. The software may be persistently stored in any type of non-volatile storage.

Figure 4:
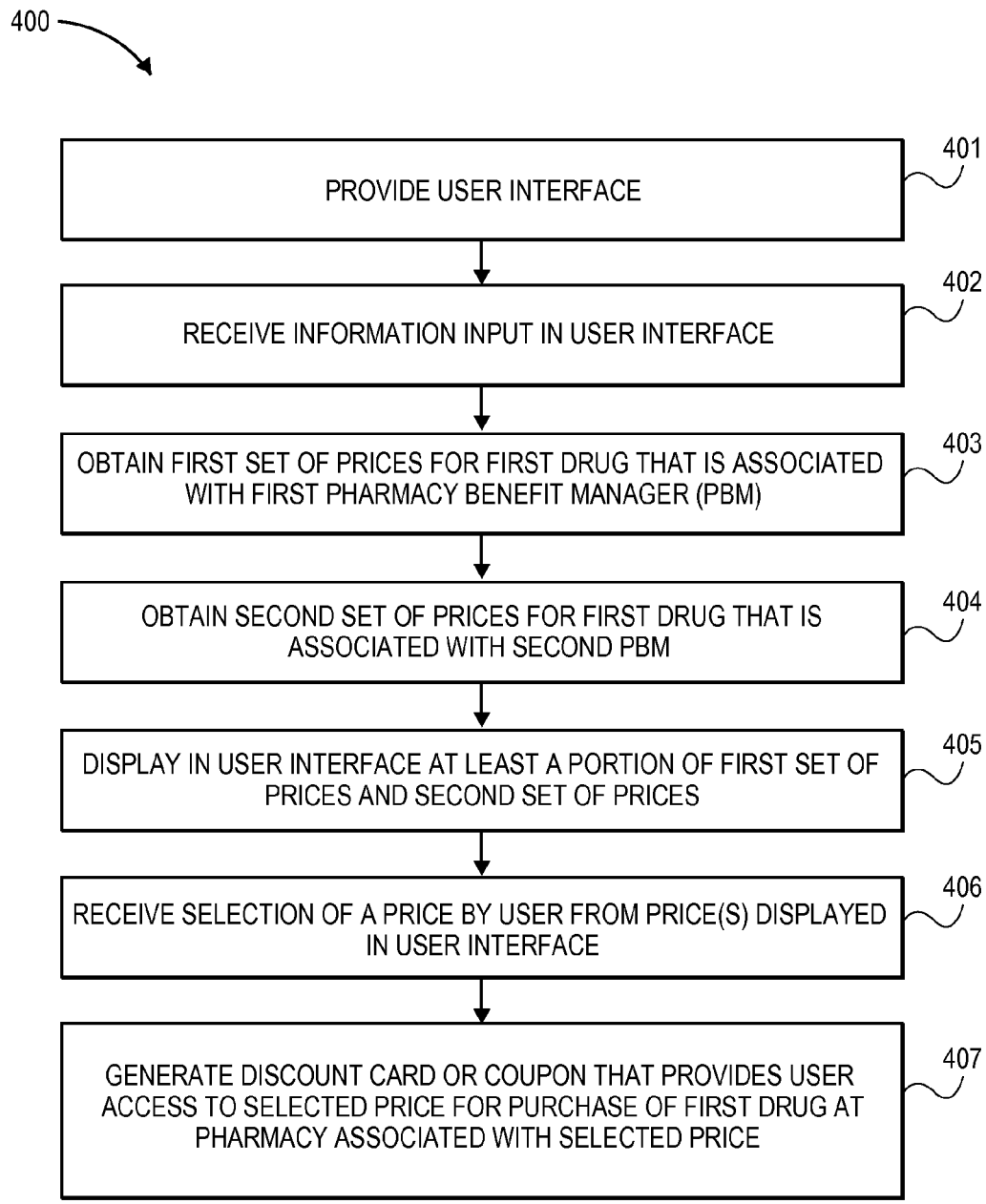
FIG. 4 illustrates another embodiment of an example process for displaying drug prices from multiple for Pharmacy Benefit Managers.

FIG. 4 illustrates another embodiment of an example process 400 for displaying drug prices from multiple for PBMs. The process 400 is described with respect to the system 200 of FIG. 2. However, one or more of the steps of process 400 may be implemented by other systems, such as the system 100 described in FIG. 1. The process 400 can be implemented by any one of, or a combination of, the components of the system 200 (e.g., the PBM module 250). Further details regarding certain aspects of at least some of steps of the process 400 are described in greater detail above with reference to FIGS. 1-3.

Blocks 401 through 405 are similar to blocks 301 through 305 in FIG. 3, respectively. Details relating to blocks 401 through 405 are described in detail with respect to FIGS. 1-3. At block 401, the system 200 provides a user interface 210. At block 402, the system 200 receives information input in the user interface 210. At block 403, the system 200 obtains a first set of prices for the first drug that is associated with a first PBM. At block 404, the system 200 obtains a second set of prices for the first drug that is associated with a second PBM. At block 405, the system 200 displays in the user interface 210 at least a portion of the first set of prices and the second set of prices.

At block 406, the system 200 receives a selection of a price from one or more prices displayed in the user interface 210. For example, the user can select a price among the prices displayed in the user interface 210.

At block 407, the system 200 generates a discount card or coupon that provides access to the selected price for a purchase of the first drug at a pharmacy associated with the selected price. Without the discount card or the discount coupon, the selected price from a PBM associated with the selected price may not available to a customer for the purchase of the first drug at the pharmacy. The discount card or the discount coupon can include an identification number that is recognized by the PBM associated with the selected price. The selected price can be provided under an agreement between an entity associated with the system 200 and the PBM associated with the selected price, where this agreement is different from an agreement between the PBM associated with the selected price and the pharmacy associated with the selected price.

In one embodiment, if an agreement between a PBM and a pharmacy specifies a price of the first drug for customers who are not members of a health insurance plan, the system 200 displays in the user interface 210 the price of the first drug for non-member customers. If the user selects the non-member price in the user interface 210, the system 200 generates a discount coupon for the purchase of the first drug at the non-member price at the pharmacy.

The process 400 can include fewer, more, or different blocks than those illustrated in FIG. 4 without departing from the spirit and scope of the description. Moreover, it will be appreciated by those skilled in the art and others that some or all of the functions described in this disclosure may be embodied in software executed by one or more processors of the disclosed components and mobile communication devices. The software may be persistently stored in any type of non-volatile storage.

Figure 5:
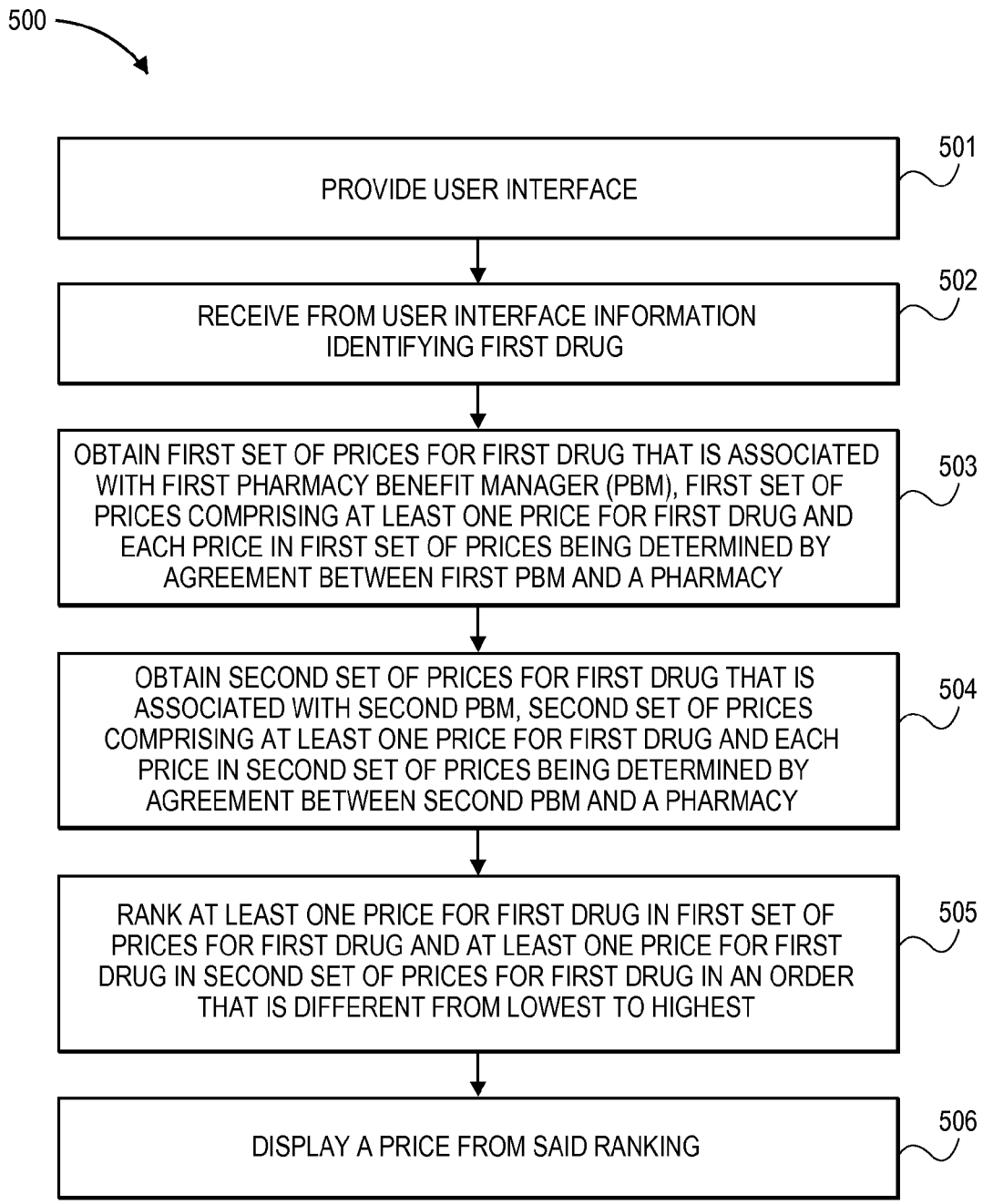
FIG. 5 illustrates one embodiment of an example process for ranking drug prices from multiple for Pharmacy Benefit Managers.

FIG. 5 illustrates one embodiment of an example process 500 for ranking drug prices from multiple for PBMs. The process 500 is described with respect to the system 200 of FIG. 2. However, one or more of the steps of process 500 may be implemented by other systems, such as the system 100 described in FIG. 1. The process 500 can be implemented by any one of, or a combination of, the components of the system 200 (e.g., the PBM module 250). Further details regarding certain aspects of at least some of steps of the process 500 are described in greater detail above with reference to FIGS. 1-4.

Blocks 501 through 504 are similar to blocks 301 through 304 in FIG. 3 and blocks 401 through 404 in FIG. 4, respectively. Details relating to blocks 501 through 504 are described in detail with respect to FIGS. 1-4. At block 501, the system 200 provides a user interface 210. At block 502, the system 200 receives from the user interface 210 information identifying a first drug. At block 503, the system 200 obtains a first set of prices for the first drug that is associated with a first PBM. At block 504, the system 200 obtains a second set of prices for the first drug that is associated with a second PBM. The first set of prices can be determined by an agreement between the first PBM and a pharmacy, and the second set of prices can be determined by an agreement between the second PBM and a pharmacy. The pharmacy for the first set of the prices and the second set of prices may be the same pharmacy or different pharmacies.

At block 505, the system 200 ranks the at least one price for the first drug in the first set of prices for the first drug and the at least one price for the first drug in the second set of prices for the first drug in an order that is different from lowest to highest.

The system 200 may determine that the at least one price for the first drug in the first set of prices is higher than (or equal to) the at least one price for the first drug in the second set of prices, but rank the at least one price in the first set of prices higher than the at least one price in the second set of prices. In one embodiment, the system 200 may rank the at least one price in the first set of prices higher than the at least one price in the second set of prices based on an acceptance rate associated with the at least one price in the first set of prices and an acceptance rate associated with the at least one price in the second set of prices. An acceptance rate may refer to the rate at which a price or prices provided by a PBM are accepted at a particular pharmacy. If a pharmacy has multiple networks with a PBM, the acceptance rates can differ for each network. Acceptance rate information may be available per drug, per group of drugs, for all drugs in a network, etc. The system 200 may rank the higher price higher when the difference between the at least one price for the first drug in the first set of prices and the at least one price for the first drug in the second set of prices does not exceed a threshold value. For example, the threshold value can be a very small number to minimize any impact on the customer price for the drug. Examples of the threshold value include $0.10, $0.20, amounts under $1, etc. The system 200 generally displays the higher ranked price from the ranking process in the user interface 210.

The system 200 may also specify a preferred order for ranking prices from the first PBM and prices from the second PBM. The preferred order can indicate that prices from the first PBM are to be ranked higher than prices from the second PBM. In general, higher ranked prices have a higher level of importance or priority. For example, higher ranked prices list may appear first in a sequence.

In one embodiment, the system 200 determines share of prices to display from a certain PBM by designating percentages for different PBMs. For example, the system 200 can determine a first percentage that indicates a portion of prices from the first PBM to be displayed in the user interface 210 and a second percentage that indicates a portion of prices from the second PBM to be displayed in the user interface 210. The ranking can be performed by ranking the at least one price for the first drug in the first set of prices and the at least one price for the first drug in the second set of prices based at least in part on the first percentage and the second percentage. A percentage may be linked to a threshold value for ranking prices from one PBM over another PBM such that adjusting the percentage adjusts the threshold value and adjusting the threshold value adjusts the percentage.

At block 506, the system 200 displays a price from the ranking in the user interface 210. For example, the highest ranked price may be listed for a specific pharmacy. The user can select a displayed price, for example, to purchase a drug at the selected price. In one embodiment, the system 200 generates a discount card or coupon that provides access to the selected price for the purchase of the first drug at a pharmacy associated with the selected price.

The process 500 can include fewer, more, or different blocks than those illustrated in FIG. 5 without departing from the spirit and scope of the description. Moreover, it will be appreciated by those skilled in the art and others that some or all of the functions described in this disclosure may be embodied in software executed by one or more processors of the disclosed components and mobile communication devices. The software may be persistently stored in any type of non-volatile storage.

Figure 6:
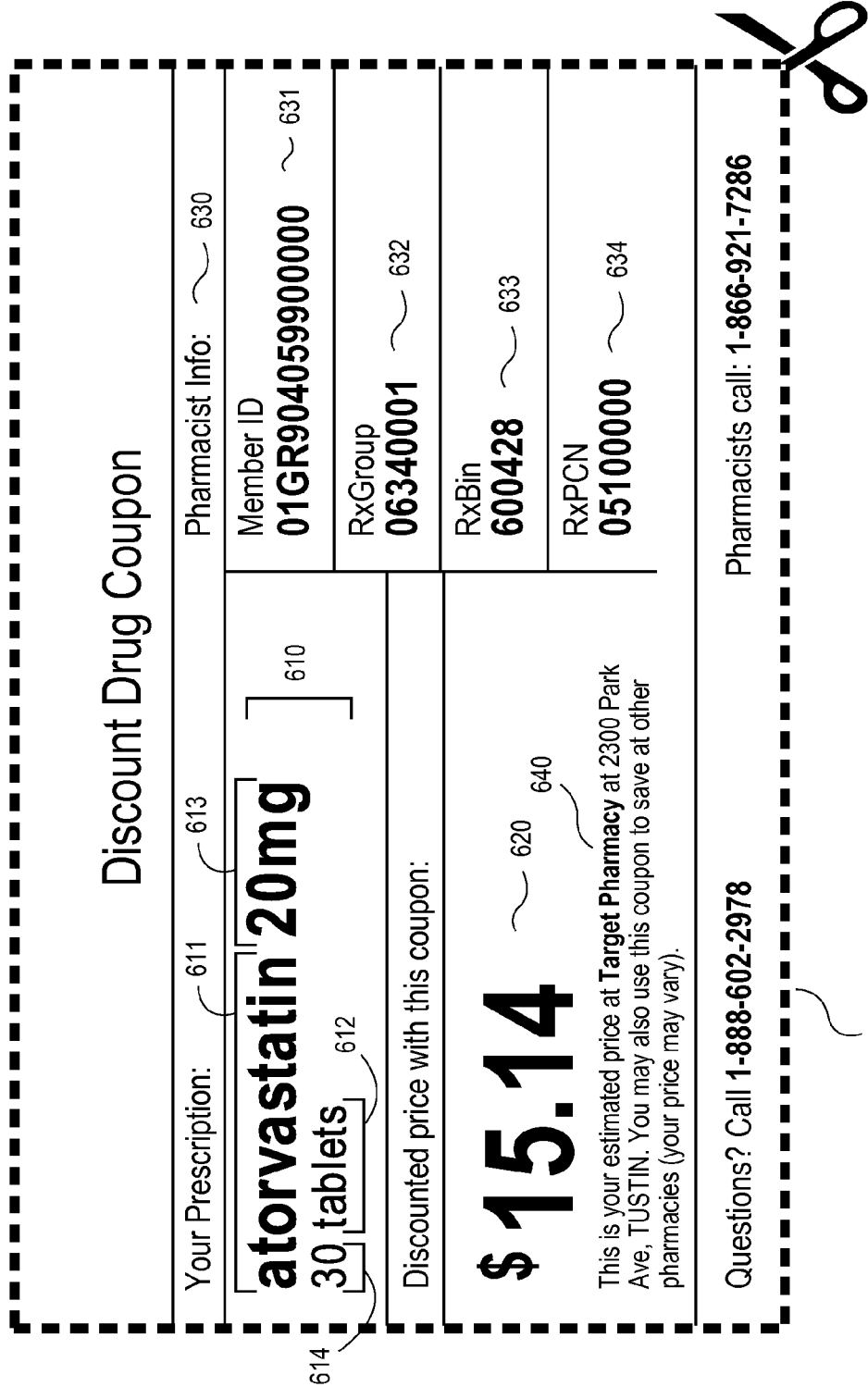
FIG. 6 illustrates one embodiment of a discount coupon.

FIG. 6 illustrates one embodiment of a discount coupon 600. Details relating to the discount coupon are explained in more detail with respect to FIGS. 1-5. Various functions relating to the discount coupon 600 can be performed by the system 100 described in FIG. 1, the system 200 described in FIG. 2, or any other appropriate system. The discount coupon 600 can be for a specific drug and may include information relating to the drug 610. Drug information 610 may include the name of the drug 611, the form of the drug 612, the dosage of the drug 613, the quantity of the drug 614, etc. The name of the drug 611 can be the generic name or the brand name. In the example of FIG. 6, the generic name of the drug 611 is atorvastatin; the form of the drug 612 is a tablet; the dosage of the drug 613 is 20 mg; and the quantity of the drug 614 is 30.

The coupon 600 may also include the price for the drug 620 for a particular pharmacy 640. A pharmacy chain may have multiple locations within a geographical area of interest, and in such case, the coupon 600 can indicate a particular pharmacy location. In FIG. 6, the pharmacy is a Target pharmacy, and the pharmacy location is at 2300 Park Avenue, Tustin, Calif. The listed price 620 for the package of the drug designated by the drug information 610 is $15.14.

The discount coupon 600 may also include the member ID 631, group number 632, bin number 633, and PCN number 634, which may be referred to collectively as "pharmacist info" 630. The pharmacist info 630 may be entered by a pharmacist at a pharmacy for the purchase of the drug. As explained above, the member ID 631 may be an identifier assigned by the system 200 under an agreement between the entity associated with the system 200 and the PBM the price 620 is provided by. A unique or rotating member ID can be assigned to a specific user. The group number 633 can identify the entity associated with the system 200. The bin number 633 and/or the PCN number 634 can identify the PBM. In one embodiment, the member ID 631 is used to identify the entity associated with the system 200. In another embodiment, a combination of the member ID 631 and the group number 632 is used to identify the entity. In the example of FIG. 6, the member ID 631 is "01GR904059900000"; the group ID 632 is "06340001"; the bin number 633 is "600428"; and the PCN number 634 is "05100000."

The discount coupon 600 can include other information, such as a phone number for a help line, a phone number for pharmacists, etc. A discount card may include similar information other than a particular pharmacy since discount cards can be accepted at multiple pharmacies.

Figure 7:
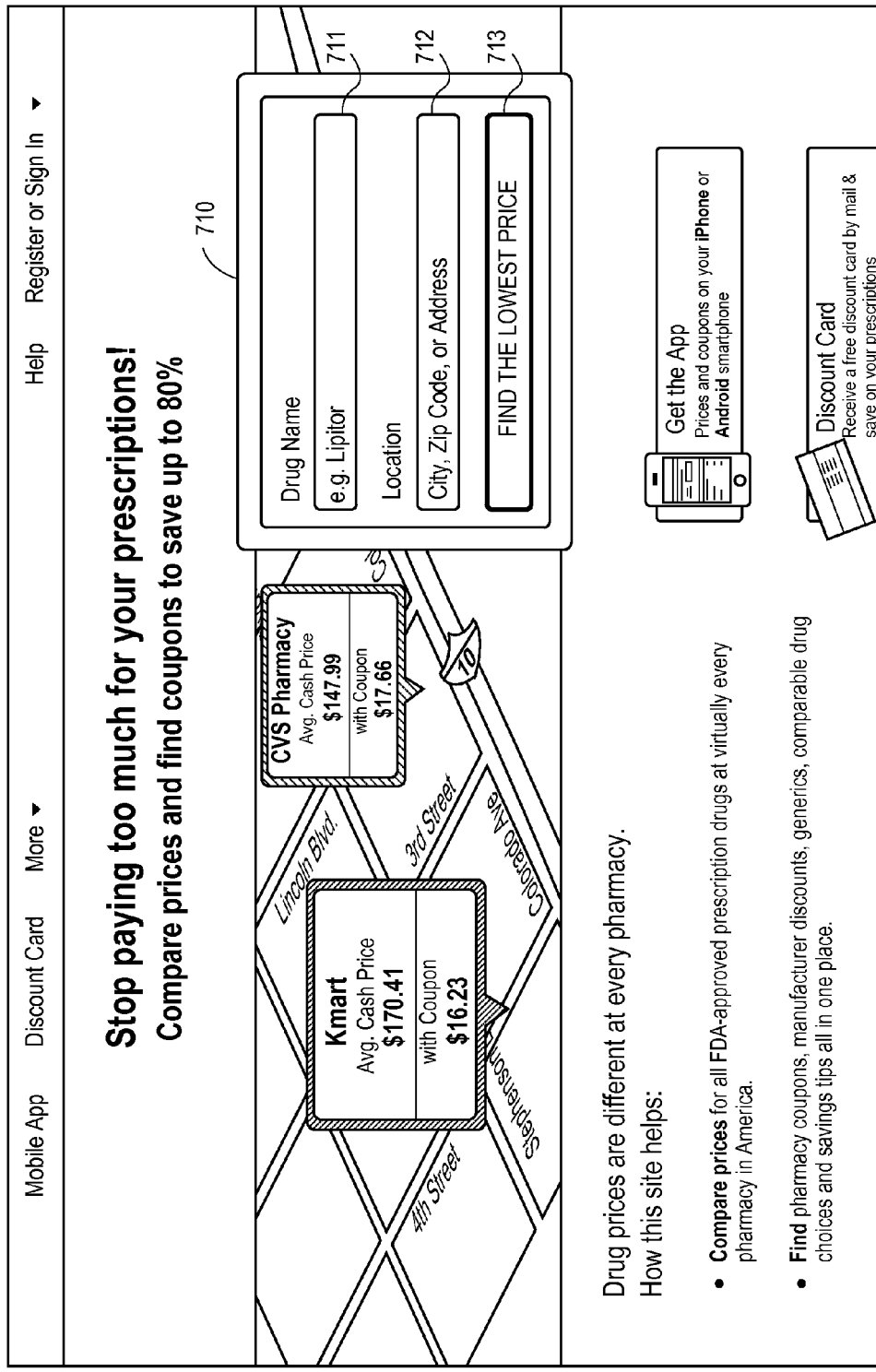
FIG. 7 illustrates one embodiment of a user interface for providing drug prices from various Pharmacy Benefit Managers.

FIG. 7 illustrates one embodiment of a user interface 700 for providing drug prices from various PBMs. Details relating to the user interface 700 are explained in more detail with respect to FIGS. 1-6. Various functions relating to the user interface 700 can be performed by the system 100 described in FIG. 1, the system 200 described in FIG. 2, or any other appropriate system. The user interface 700 is provided to receive information relating to a drug from a user. The user interface 700 may be a web user interface. The user interface 700 can include a section for entering the drug information 710. In one embodiment, the section 710 includes an input field for drug name 711 and an input field for location 712. The section 710 also includes a button 713 for generating a request for pricing information for the drug name 711 entered by the user. The drug name field 711 can display the name of a common drug as a suggestion to provide users with some guidance on entering drug names. In one embodiment, the user can enter a health condition (e.g., asthma) in the drug name field 711 to view prices for drugs related to the health condition. In some embodiments, as the user types the drug name, the drug name field 711 shows a list of drug names that include the typed letters and/or shows related drug names or conditions for the entered drug name. The location input field 712 can accept various types of input, such as city, zip code, address, etc.

The example user interface 700 in FIG. 7 may also include various menu items. Some examples include a menu item for downloading a mobile application for requesting drug prices from the system 200, a menu item for applying for a discount card, a menu item for registering to become of a member of the system 200, and a menu item for signing in for registered members. The system 200 can store information for registered members, such as drugs purchased by members using discount coupons provided by the system 200. The system 200 can also provide additional features, such as providing price alerts, prescription fill alerts, etc.

Figure 8:
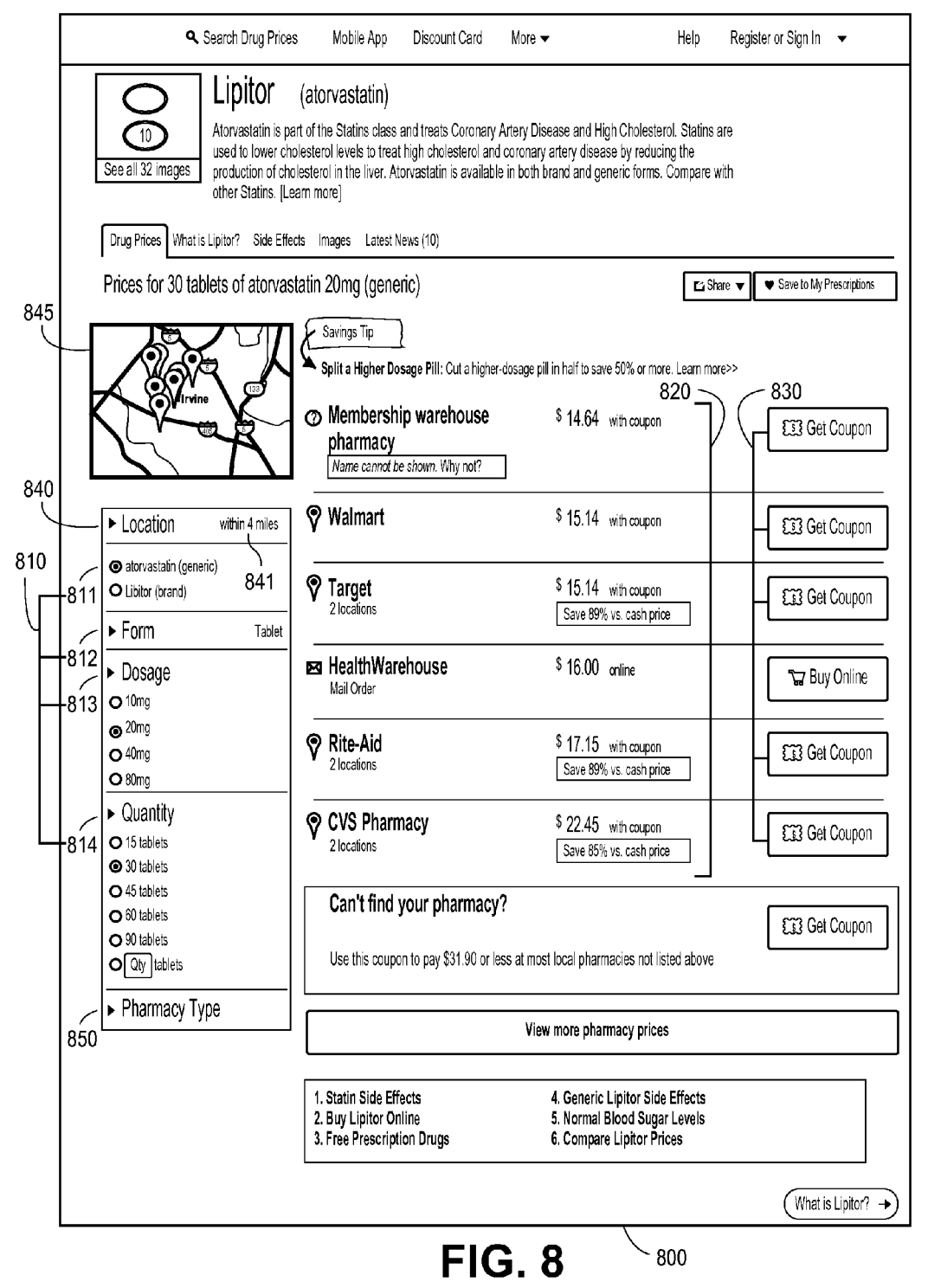

FIG. 8 illustrates another embodiment of a user interface 800 for providing drug prices from various PBMs. Details relating to the user interface 800 are explained in more detail with respect to FIGS. 1-7. Various functions relating to the user interface 800 can be performed by the system 100 described in FIG. 1, the system 200 described in FIG. 2, or any other appropriate system. The user interface 800 is provided to display drug prices and/or information relating to a specific drug. As explained with respect to FIG. 7, the user may enter the drug name and the location information and send a request for pricing information for a specific drug. In response to the request, the user interface 800 can provide drug prices for the drug. The user interface 800 may display drug information 810, such as the name of the drug 811, the form of the drug 812, the dosage of the drug 813, the quantity of the drug 814, etc. The name of the drug 811 can be the generic name, brand name, or both. The drug information 810 can be for a specific package of the drug (e.g., the most common package).

When there is more than one type of package available for a drug, the user interface 800 can display various options for indicating a particular package of the drug. For example, the system 200 can provide options for generic or band version 811, options for form 812, options for dosage 813, options for quantity 814, etc. The user can select an appropriate option for each category to select the package of the drug that the user wants. In the example of FIG. 8, atorvastatin is available as generic or brand version, and the generic name and the brand name of the drug are provided as options for the drug name 811. The only option for form 812 is tablet. The options for dosage 813 are 10 mg, 20 mg, 40 mg, and 80 mg. The options for quantity 814 are 15 tablets, 30 tablets, 45 tablets, 60 tablets, and 90 tablets. The user interface 800 also provides an input field for entering a desired quantity 814. The options corresponding to the package for which the prices are currently displayed are selected under each category. In this example, the prices 820 are for the generic version atorvastatin in tablet form having 20 mg dosage in quantity of 30 tablets, and these options are marked in the user interface 800. The user can select any of the options provided under each category to designate a combination of options that the user is interested in.

The user interface 800 may also display prices 820 for the drug available from one or more pharmacies. The prices 820 may be for the most common or user selected package for the drug. In one embodiment, the user interface 800 displays a default number of prices, and if there are any additional prices not displayed, provides a link or a button to show the additional prices. In the example of FIG. 8, each price 820 is associated with one pharmacy. If there is more than one price for each pharmacy, the multiple prices for the pharmacy may have been ranked according to a lowest to highest algorithm or another ranking method as discussed above. The system 200 can display one price for each pharmacy, for example, the highest ranked price. The price 820 for Walmart is $15.14 with a discount coupon. The price 820 for Target is also $15.14 with a discount coupon. The price 820 for HealthWarehouse, an online pharmacy, is $16.00 without a discount coupon, and so on. In the example of FIG. 8, the prices 820 from different pharmacies are listed in the order of lowest to highest. For a price 820 that is available through a discount coupon, the user interface 800 displays a button 830 for obtaining a discount coupon for that price 820. The coupon can be accepted at the pharmacy associated with the price 820. Details relating to the coupon are explained in more detail with respect to FIGS. 1-7.

In some embodiments, the user may not see a price 820 listed for a pharmacy of the user's interest, and the system 200 provides a generic discount coupon that can be used at pharmacies not listed in the user interface 800. Such pharmacies may be independent pharmacies not associated with large pharmacy chains. PBMs may provide prices for such independent pharmacies to the entity associated with the system 200.

The user interface 800 can also display the location information 840 relating to the prices 820. The location information 840 can be entered by the user. The user interface 800 may also indicate the default radius 841 for including pharmacy locations relating to the location information 840. In FIG. 8, the default radius 841 is listed as 4 miles. The user can change the radius 841 as appropriate. For example, the user can select from a list of options in a drop-down menu. The user may be able to change the location information 840 after the prices 820 are initially displayed, and the displayed prices 820 can change based on the location information 840. The user interface 800 can provide an input field for entering a new city, zip code, address, etc. The user interface 800 may also provide a map 845 showing a region that includes the pharmacy locations for the prices 820 displayed in the user interface 800. As the user updates the location information 840 or the default radius 841, the map 845 can change to reflect the updated information.

The user interface 800 may also display pharmacy options 850. As explained above, the user can choose which types of pharmacies to view prices for. Some examples of pharmacy options or types include: 24-hour, mail order, home delivery, compounding, walk-in clinic, drive-up window, languages spoken, major chains, etc.

The example user interface 800 in FIG. 8 may also include other types of information relating to the drug, such as a description of the drug, side effects, images of the drug, news relating to the drug, advertisements relating to the drug, etc. The user interface 800 can also provide other useful information, such as savings tips.

The various illustrative processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various processes described herein may be implemented or performed by a machine, such as a computer, a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor, a controller, microcontroller, state machine, combinations of the same, or the like. A processor may also be implemented as a combination of computing devices, e.g., a combination of a DSP and a microprocessor, a plurality of microprocessors or processor cores, one or more graphics or stream processors, one or more microprocessors in conjunction with a DSP, or any other such configuration.

The processes described herein may be embodied directly in hardware, in a software module executed by a processor, or in a combination of the two. For example, each of the processes described above may also be embodied in, and fully automated by, software modules executed by one or more machines such as computers or computer processors. A module may reside in a computer-readable storage medium such as RAM memory, flash memory, ROM memory, EPROM memory, EEPROM memory, registers, hard disk, a removable disk, a CD-ROM, memory capable of storing firmware, or any other form of computer-readable storage medium known in the art. An exemplary computer-readable storage medium can be coupled to a processor such that the processor can read information from, and write information to, the computer-readable storage medium. In the alternative, the computer-readable storage medium may be integral to the processor. The processor and the computer-readable storage medium may reside in an ASIC.

Depending on the embodiment, certain acts, events, or functions of any of the processes or algorithms described herein can be performed in a different sequence, may be added, merged, or left out all together. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the logical blocks, modules, and processes illustrated may be made without departing from the spirit of the disclosure. As will be recognized, certain embodiments of the inventions described herein may be embodied within a form that does not provide all of the features and benefits set forth herein, as some features may be used or practiced separately from others.

What is claimed is:

1. A method of displaying prices for drugs from a plurality of pharmacy benefit managers, the method comprising:

providing a user interface using a computer processor;

receiving from the user interface information identifying a first drug;

obtaining a first set of prices for the first drug that is associated with a first pharmacy benefit manager (PBM), wherein a pharmacy benefit manager processes a claim relating to a drug and has an agreement with a pharmacy relating to a price of one or more drugs, the first set of prices comprising at least one price for the first drug and each price in the first set of prices being determined by an agreement between the first PBM and a pharmacy;

obtaining a second set of prices for the first drug that is associated with a second pharmacy benefit manager, the second set of prices comprising at least one price for the first drug and each price in the second set of prices being determined by an agreement between the second PBM and a pharmacy; and displaying in the user interface at least a portion of the first set of prices and the second set of prices.

2. The method of claim 1, further comprising:
receiving a selection of a price from the at least a portion of the first set of prices and the second set of prices displayed in the user interface; and
generating a discount card or a discount coupon that provides access to the selected price for a purchase of the first drug at a pharmacy associated with the selected price.

3. The method of claim 2, wherein the selected price is not available to a customer for the purchase of the first drug at the pharmacy from a PBM associated with the selected price without the discount card or the discount coupon.

4. The method of claim 3, wherein the selected price is provided under an agreement with the PBM associated with the selected price, the agreement being different from an agreement between the PBM associated with the selected price and the pharmacy associated with the selected price.

5. The method of claim 2, wherein the discount card or the discount coupon comprises an identification number that is recognized by a PBM associated with the selected price.

6. The method of claim 1, wherein:
the first PBM administers claims relating to a first health insurance plan, and an agreement between the first PBM and a first pharmacy specifies a price of the first drug for a member of the first health insurance plan and a first price of the first drug for a customer that is not a member of the first health insurance plan, the first set of prices comprising the first price of the first drug for a customer that is not a member of the first health insurance plan; and
the second PBM administers claims relating to a second health insurance plan, and an agreement between the second PBM and a second pharmacy specifies a price of the first drug for a member of the second health insurance plan and a second price of the first drug for a customer that is not a member of the second health insurance plan, the second set of prices comprising the second price of the first drug for a customer that is not a member of the second health insurance plan.

7. The method of claim 6, further comprising:
displaying in the user interface the first price of the first drug for a customer that is not a member of the first health insurance plan; and
in response to selection of the first price received from the user interface, generating a discount coupon for a purchase of the first drug at the first price at the first pharmacy.

8. The method of claim 1, wherein the information identifying the first drug comprises a name of the first drug.

9. The method of claim 1, further comprising:
receiving from the user interface location information; and
prior to said displaying at least a portion of the first set of prices and the second set of prices, filtering the first set of prices and the second set of prices based on the location information.

10. The method of claim 1, wherein the at least one price in the first set of prices is obtained by using an API provided by the first PBM.

11. The method of claim 1, wherein the at least one price in the first set of prices is obtained based on pricing rules for the first drug provided by the first PBM.

12. The method of claim 1, wherein the first set of prices comprises a first price for the first drug determined by an agreement between the first PBM and a first pharmacy and the second set of prices comprises a second price for the first drug determined by an agreement between the second PBM and the first pharmacy,
wherein said displaying at least a portion of the first set of prices and the second set of prices comprises:
comparing the first price for the first drug and the second price for the first drug; and
displaying lower of the first price for the first drug and the second price for the first drug.

13. A system for displaying prices for drugs from a plurality of pharmacy benefit managers, the system comprising:
computer hardware comprising one or more computer processors; and
a module executing on the one or more computer processors and configured to:
receive a request for one or more prices for a first drug;
obtain a first set of prices for the first drug that is associated with a first pharmacy benefit manager (PBM), wherein a pharmacy benefit manager processes a claim relating to a drug and has an agreement with a pharmacy relating to a price of one or more drugs, the first set of prices comprising at least one price for the first drug and each price in the first set of prices being determined by an agreement between the first PBM and a pharmacy;
obtain a second set of prices for the first drug that is associated with a second pharmacy benefit manager, the second set of prices comprising at least one price for the first drug and each price in the second set of prices being determined by an agreement between the second PBM and a pharmacy; and
display in the user interface at least a portion of the first set of prices and the second set of prices.

14. The system of claim 13, wherein the module is further configured to:
receive a selection of a price from the at least a portion of the first set of prices and the second set of prices displayed in the user interface; and
generate a discount card or a discount coupon that provides access to the selected price for a purchase of the first drug at a pharmacy associated with the selected price.

15. The system of claim 14, wherein the selected price is not available to a customer for the purchase of the first drug at the pharmacy from a PBM associated with the selected price without the discount card or the discount coupon.

16. The system of claim 15, wherein the selected price is provided under an agreement with the PBM associated with the selected price, the agreement being different from an agreement between the PBM associated with the selected price and the pharmacy associated with the selected price.

17. The system of claim 14, wherein the discount card or the discount coupon comprises an identification number that is recognized by a PBM associated with the selected price.

18. The system of claim 13, wherein:
the first PBM administers claims relating to a first health insurance plan, and an agreement between the first PBM and a first pharmacy specifies a price of the first drug for a member of the first health insurance plan and a first price of the first drug for a customer that is not a member of the first health insurance plan, the first set of prices comprising the first price of the first drug for a customer that is not a member of the first health insurance plan; and
the second PBM administers claims relating to a second health insurance plan, and an agreement between the second PBM and a second pharmacy specifies a price of the first drug for a member of the second health insurance plan and a second price of the first drug for a customer that is not a member of the second health insurance plan, the second set of prices comprising the second price of the first drug for a customer that is not a member of the second health insurance plan.

19. The system of claim 18, wherein the module is further configured to:
   display in the user interface the first price of the first drug for a customer that is not a member of the first health insurance plan; and
   in response to selection of the first price received from the user interface, generate a discount coupon for a purchase of the first drug at the first price at the first pharmacy.

20. The system of claim 13, wherein the first set of prices comprises a first price for the first drug determined by an agreement between the first PBM and a first pharmacy and the second set of prices comprises a second price for the first drug determined by an agreement between the second PBM and the first pharmacy,
   wherein the module performs said displaying at least a portion of the first set of prices and the second set of prices at least in part by:
      comparing the first price for the first drug and the second price for the first drug; and
      displaying lower of the first price for the first drug and the second price for the first drug.

* * * * *